United States Patent [19]
Roninson et al.

[11] Patent Number: 6,060,244
[45] Date of Patent: May 9, 2000

[54] GENES AND GENETIC ELEMENTS ASSOCIATED WITH SENSITIVITY TO CHEMOTHERAPEUTIC DRUGS

[76] Inventors: Igor B. Roninson, 2731 Lincoln La., Wilmette, Ill. 60091; Andrei Gudkov, 5740 S. Maryland, Apt. 2, Chicago, Ill. 60637

[21] Appl. No.: 08/929,208

[22] Filed: Sep. 9, 1997

Related U.S. Application Data

[62] Division of application No. 08/480,552, Jun. 7, 1995, Pat. No. 5,665,550, which is a continuation of application No. 08/033,086, Mar. 9, 1993, abandoned, which is a continuation-in-part of application No. 08/039,385, filed as application No. PCT/US91/07492, Oct. 11, 1991, which is a continuation-in-part of application No. 07/599,730, Oct. 19, 1990, Pat. No. 5,217,889.

[51] Int. Cl.$^7$ .................................................. C12Q 1/68
[52] U.S. Cl. ................. 435/6; 435/7.1; 530/324; 530/325; 530/326; 530/327; 530/328; 530/329; 530/388.26; 530/388.9
[58] Field of Search .............................. 435/6, 7.1, 172.3, 435/440; 530/324–329, 388.26, 388.9

[56] References Cited

U.S. PATENT DOCUMENTS 5,217,889  6/1993  Roninson et al. ........................ 435/6

OTHER PUBLICATIONS

Herskowitz, *Nature*, vol. 329, 1987, pp. 219–222.
Trono et al., *Cell*, vol. 59, Oct. 1989, pp. 113–120.
Friedman et al., Nature, vol. 335, Sep. 1988, pp. 452–454.
Chen et al. Cell 47:381–389 (1986).
Holzmayer et al. Nucleic Acids Res 20: 711–717 (1992).
Gudkov et al. Proc. Natl. Acad Sci.(1993).
Uhlmann and Peyman Chemical Reviews 90: 543–584 (1990).
Schneider & Banner, Tethrahedron Letters 31:335 (1990).
Culver et al. Science 256:1550–1552 (1992).
Miller & Rosman, Biotechniques 7:980–986 (1989).
Bodine et al Proc Natl Acad Sci USA 87:3738–3742 (1990).
Baim et al. Proc Natl Acad Sci USA 88:5072–5076 (1991).
Endow, Trends Biochem Scie 16: 221–225 (1991).
Navone et al. J Cell Biol 117: 1263–1275 (1992).
Lau and Nathans, EMBO J. 4:3145–3151 (1985).
Lau and Nathans, Proc. Natl Acad Sci USA 84:1182–1186 (1987).
Noonan et al Proc Natl Acad Sci USA 87:7160–7164 (1990).
Tsai–Pflugfleder et al. Proc. Natl. Acad. Sci USA 85:7177–7181 (1988).
Markowitz et al., Virology 167: 400–406 (1988).
Baltimore et al., Nature 335:395–396 (1988).
Green et al., Cell 58:215–223.
Rimsky et al., Nature 341: 453–456 (1989).
Trono et al., Cell 59:113–120 (1989).
Ransone et al., Proc. Natl. Acad. Sci. USA 87:3806–3810 (1990).
Whitaker–Dowling et al., Virology 175:358–364 (1990).
Lee et al., J. Bacteriol 171:3002–307 (1989).
Chejanovsky et al., J. Virol. 64: 1764–1770 (1990).
van der Krol et al., Biotechniques 6:958–976 (1988).
Ch'ng et al., Proc. Natl. Acad. Sci. 86: 10006–10010 (1989).
Daugherty et al., Gene Anal. Tech. 6:1–16 (1989).
Powell et al., Proc. Natl. Acad Sci, USA 86: 6949–6952 (1989).
Sarver et al., Science 247:1222–1225 (1990).
Kerr et al., Eur. J. Biochem 175:65–73 (1998).
Bunnell et al., Somat. Cell Mol. Genet. 16: 151–162 (1990).
Keown et al., Methods Enzymol 185: 527–536 (1990).
Miller and Rosman, Biotechniqes 1:980–986(1989).
Murphy and Efstatiadis, Proc. Natl. Acad. Sci. USA 84:8277–8281.
Davis et al., Microbiology, Harper and Row, Philadelphia, PA (1980).
Patterson et al., Methods Enzymol 151:121(1982).
Groger et al., Gene 81:285–294 (1989).
Rio et al., Science 227:23–28 (1985).
Kosak and Kabat, J. Virol 64 3500–3508 (1990).
Gussow et al., J. Immunol. 139: 3132–3138 (1987).
Patanjali et al., Proc. Natl. Acad. Sci. USA 88:1943–1947(1991).
Ohara et al., Proc. Natl. Acad. Sci. USA 86:5673–5677 (1989).
Kato J., Neurosci 2: 704–711 (1991).
Kosik et al., J. Biol. Chem. 265: 3278–3283 (1990).
Murphy & Schmike Nucleic Acids Res. 19: 3403–3408 (1991).
Kim et al., J. Biol. Chem 267: 23113–23121.
Lock et al., J. Cancer 42(3): 371–381(1988).
Shen et al., Science 232:643–645 (1986).
Sczakiel G. et al. Bioch. Biophys. Res. Comm. 169(2):643–651 (1990).
Napoli C., The Plant Cell 2(4):279–289(1990).
Kidd V.J. et al., Chemical Abstracts 111(23).
Baird et al., J. Bacteriol 172:1587–1594 (1990).
Fereira et al., J. Cell Biol 117:595–606 (1992).
Deiss et al., Science vol. 252:117–120 (1991).

*Primary Examiner*—James Ketter
*Attorney, Agent, or Firm*—McDonnell Boehnen Hulbert & Berghoff

[57] ABSTRACT

The invention provides genetic suppressor elements that confer upon a cell resistance to one or more chemotherapeutic drug, methods for identifying and obtaining such elements, and methods of using such elements. The invention also provides cloned genes associated with sensitivity to chemotherapeutic drugs.

7 Claims, 40 Drawing Sheets

FIG. 1A

```
GTGTCTGGGC GGAGCAAAAT ATGTTCCAAT TGTGTTTTCT TTTGATAGAT TCTTTCAACA   60
GACAGTCTTT TCTTAGCATC TTCATTTTTC TTTATTTTGT TGACTTGCAT ATTTTCATTT  120
ACAGGCTGCA ATGGTGACAC TTCCATGGTG ACGGTCGTGA AGGG                   164
```

FIG. 1B

```
TGAAAAGATG TATGTCCCAG CTCTCATATT TGGACAGCTC CTAACTTCTA GTAACTATGA    60
TGATGATGAA AAGAAAGTGA CAGGTGGTCG AAATGGCTAT GGAGCCAAAT TGTGTAAACAT  120
ATTCAGTACC AAATTTACTG TGGAAACAGC CAGTAGAGAA TACAAGAAAA TGTTCAAACA  180
GACATGGATG GATAATATGG GAAGAGCTGG TGA                                213
```

FIG. 1C

```
GCCCATTGGT CAGTTTGGTA CCAGGCTACA TGGTGGCAAG GATTCTGCTA GTCCACGATA   60
CATCTTTACA ATGCTCCAGCT CTTTGGCTCG ATTGTTATTT CCACCAAAAG ATGATCACAC  120
GTTGAAGTTT TTATATGATG ACAACCAGCG TGTTGAGCCT GAATGGTACA TTCCTATTAT  180
T                                                                 181
```

FIG. 1D

```
TGAATGGTAC ATTCCTATTA TTCCCATGGT GCTGATAAAT GGTGCTGAAG GAATCGGTAC    60
TGGGTGGTCC TGCAAAATCC CCAACTTTGA TGTGCCGTGAA ATTGTAAATA ACATCAGGCG   120
TTTGATGGAT GGAGAAGAAC CTTTGCCAAT GCTTCCAAGT TACAAGAACT TCAAGGGTAC   180
TATTGAAGAA CTGGCTCCAA ATCAATATGT GATTAGTGGT GAAG                   224
```

FIG. 1E

```
TGCGTGAAAT TGTAAATAAC ATCAGGGCGTT TGATGGATGG AGAAGAACCT TTGCCAATGC    60
TTCCAAGTTA CAAGAACTTC AAGGGTACTA TTGAAGAACT GGCTCCAAAT CAATATGTGA   120
TTAGTGGTGA AGTAGCTATT CTTAATTCTA CAACCATTGA AATCTCAGAG CTTCCCGTCA   180
GAACATGGAC CCAGACATAC AAAGAACAAG TTCTAGAACC CATGTTGAAT GGCACCGAGA   240
AGACACCTCC TCTCATAACA GACTATAGGG AATACCATAC AGATACCACT GTGAAATTTG   300
TTGTGAAGAT GACTGAAGAA AAACTGGCA                                     329
```

FIG. 1F

```
CACTCTTTTC AGTTTCCTTT TCGTTGTCAC TCTCTTCATT TTCTTCTTCA TCTGGAACCT   60
TTTGCTGGGC TTCTTTCCAG GCCTTCACAG GATCCGAATC ATATCCCCTC TGAATCAGAA  120
CTTTAATTAA TTCTTTCTTA GGCTTATTTT CAATGATTAT TTTGCCATCT ATTTTCTCTA  180
AGATAAAGCG AGCC                                                    194
```

FIG. 1G

```
TCTGCCTCTG CTTTCATTTC TATGGTTATT CGTGGAATGA CTCTTTGACC ACGCGGAGAA    60
GGCAAAACTT CAGCCATTTG TGTTTTTTTC CCCTTGGCCT TCCCCCCTTT CCCAGGAAGT   120
CCGACTTGTT CATCTTTGTTT TTCCTTGGCT TCAACAGCCT CCAATTCTTC AATAAATGTA  180
GCCAAGTCTT CTTTCCACAA ATCTGA                                        206
```

FIG. 1H

```
GACACGACAC TTTTCTGTGG TTTCAGTTCT TTGTTACTAA GTTTTGGGGA AGTTTTGGTC    60
TTAGGTGGAC TAGCATCTGA TGGGACAAAA TCTTCATCAT CAGTTTTTTC ATCAAAATCT   120
GAGAAATCTT CATCTGAATC CAAATCCATT GTGAATTTTG TTTTTGTTGC TGCTCTCCGT   180
GGCTCTGTTT CTCG                                                    194
```

FIG. 11

```
CTGAAACCAC AGAAAAGTGT CGTGTCAGAC CTTGAAGCTG ATGATGTTAA GGGCAGTGTA   60
CCACTGTCTT CAAGCCCTCC TGCTACACAT TTCCCAGATG AAACTGAAAT TACAAACCCA  120
GTTCCTAAAA AGAATGTGAC AGTGAAGAAG ACAGCAGCAA AAAGTCAGTC TTCCACCTCC  180
ACTACCGGTG CCAAAAAAAG GGCTGCCCCA AAAGGAACTA AAAGGGATCC AGCTTTGAAT  240
TC                                                                 242
```

FIG. 1J

```
AATTCAAAAGC TGGATCCCTT TTAGTTCCTT TTGGGGCAGC CCTTTTTTTG GCACCGGTAG    60
TGGAGGTGGA AGACTGACTT TTTGCTGCTG TCTTCTTCAC TGTCACATTC TTTTTAGGAA   120
CTGGGTTTGT AATTTCAGTT TCATCTGGGA AATGTGTAGC AGGAGGGCTT GAAGACAGTG   180
GTACACTGCC CTTAACATCA TCAGCTTCAA GGTCTGACAC                         220
```

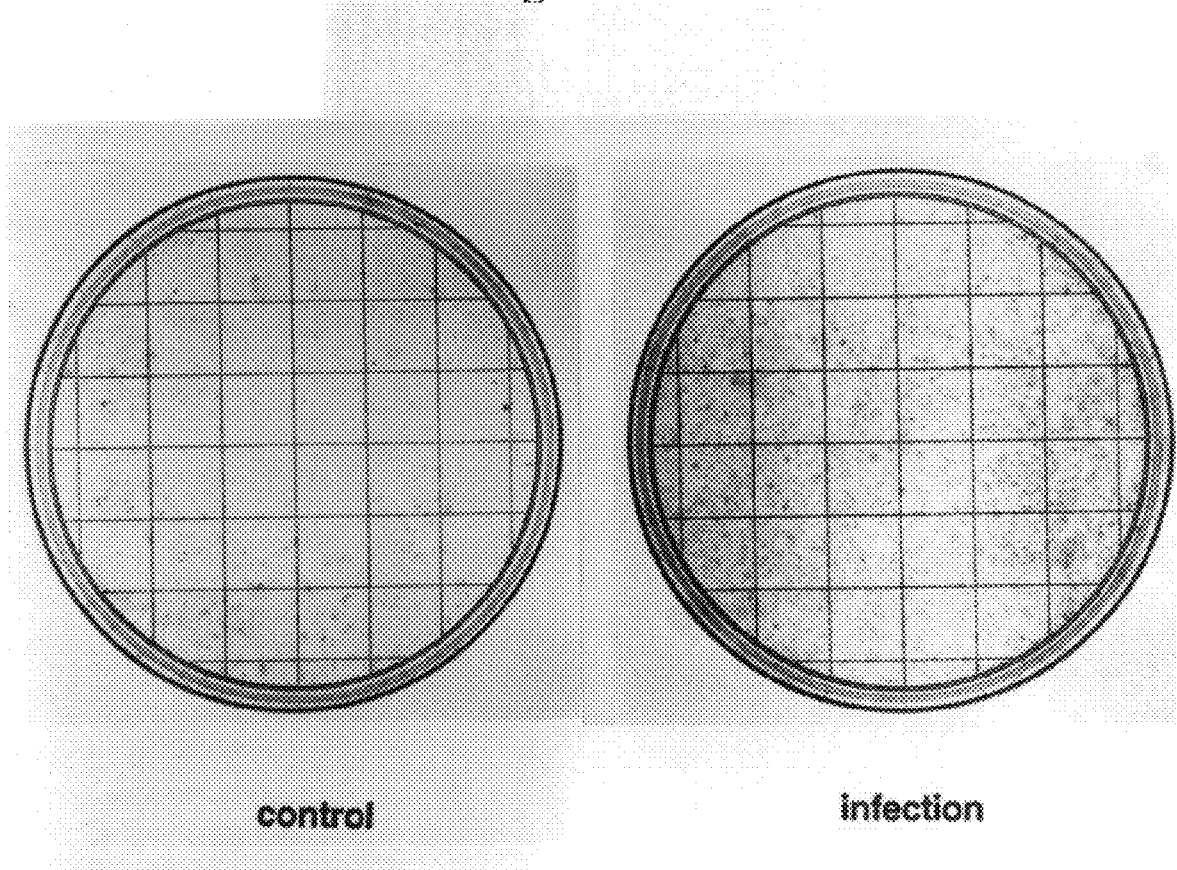

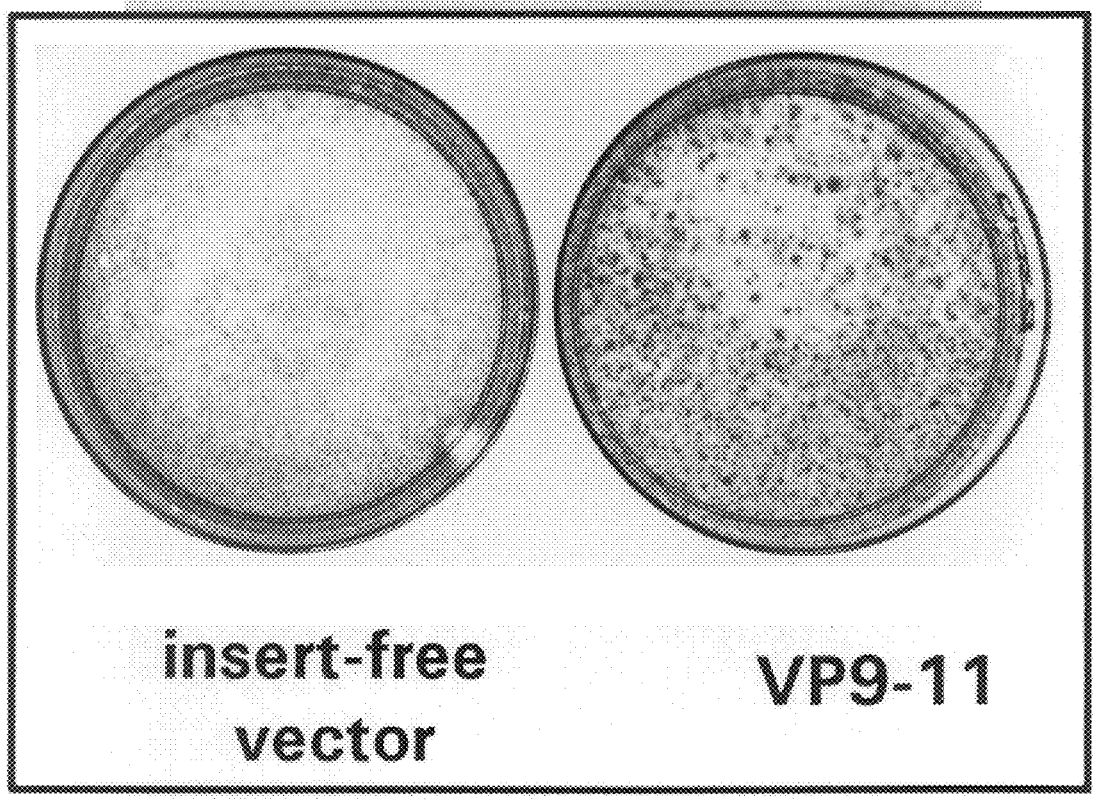

FIG. 9

```
CTTGATCCCT TCTGGTTGAT GCCAGAAGCT CTTCCTGATC CAGCATTTGT ATCTTCAATT   60
TCTCTACCAA TTGGCTTTGT TGGTTAATCT CTTCATCCTT GTCATCAAGT TGTTTATACA  120
ATTTAGCAAG TTCTTCTTCA CACTTTCTTC TTTCAGCATC GGTAAAACTA CCAGCCATTC  180
CGACTGCAGC AGCTGGTTTA TCACTGGTAA TAGCAATATC TTTATCCGCT GTGAAGGCTT  240
CCAAATTAGC TTTCTCTTTG TCAAACTGCT CATCAATAGG CACTGTCTCC CCGTTACGCC  300
AACGGTTTAG CTCGTTTTCC AGCCACT                                     327
```

FIG. 10

```
CCGACCGGGA GCGGGGAGAAG GAGCGGGGAGC GGGAGCAGCG GGAGAAGGAGG CGGGAGAAGG     60
AGCTGGAGCG CGACGGGAGA AGGAACGGGA GCGCGAGCTG GAGCGGCAGC GGGAGCAGCG    120
GGCGAGGGAG AAGGAGCTGC TGGCTGCCAA GGCCTTAGAG CCCACCACCT TCCTGCCTGT    180
GGCCGAGCTG CACGGACTCC GAGGTCACAG CACGGAGGAG CGGCCCAAGC CCTCGGAGCA    240
GCTGACCCCA                                                           250
```

FIG. 11

```
CTCAGAGGTG ATCCTCTCGG AGTCGAGCTC AGGAGAAGGA GTCCCCTTCT TTGAGACTTG    60
GATGCAGACC TGCATGTCCG AGGAGGGCAA GATTTTGAAC CCTGACCATC CCTGCTTCCG   120
CCCTGACTCC ACCGAAGTCG AGTCCTTGGT GGCCCTGCTC AACAACTCTT CAGAGATGAA   180
GCTAGTACAG ATGAAGTAGC ACGAGGCC                                      208
```

FIG. 12A

```
CGACAAACAT CATCTGGGAA GACCCACACG ATGGAGGGTA AACTTCATGA TCCAGAAGGC    60
ATGGGAATTA TTCCAAGAAT AGTGCAAGAT ATTTTTAATT ATATTTACTC CATGGATGAA   120
AATTTGGAAT TTCATATATTAA GGTTTCATAT TTTGAAATAT ATTTGGATAA GATAAGGGAC  180
TTGTTAGATG TTTCAAAGAC TAACCTTTCA GTCCATGAAG ACAAAAACCG TGTTCCCTAT   240
GTAAAGGGGT GCACAGAACG TTTCGTGTGT AGTCCAGATG AAGTCATGGA TACCATAGAT   300
GAAGGGAAAT CCAACAGAGA TGTCGCAGTT ACAAATATGA ATGAACATAG CTCTAGGAGC   360
CACAGCATAT TTCTTATTAA TGTAAAACAA GAGAATACAC AAACGGAACA GAAACTCAGT   420
GGAAAGCTTT ATCTGGTTGA TTTAGCTGGC AGTGAGAAGG TTAGTAAGAC TGGGGCTGAA   480
GGTGCTGTGC TGGATGAAGC TAAGAACATC AAGAAGTCAC TTTCTGCACT TGGAAATGTC   540
ATTTCTGCTT TGGCAGAGGG CAGTACCTAT GTTCCTTATC GAGATAGTAA AATGACCAGA   600
ATTCTTCAAG ATTCATTAGG TGGCAACTGT AGGACCACTA TTGTCATATG CTGCTCTCCA   660
TCATCATACA ATGAGTCTGA GACAAAGTCA ACACTCCCTCT TTGGTCAAAG GGCCAAAACA   720
ATTAAGAACA CAGTCTGTGT CAATGTAGAG TTAACTGCAG AGCAGTGGAA AAAGAAGTAT   780
```

FIG. 12B

```
GAAAAAGAAA AGGAAAAAAA TAAGACTCTA CGGAACACTA TTCAGTGGCT GGAAAACGAG   840
CTAAACCGTT GGCGTAACGG GGAGACAGTG CCTATTGATG AGCAGTTTGA CAAAGAGAAA   900
GCTAATTTGG AAGCCTTCAC AGCGGATAAA GATACTGCTA TTACCAGTGA TAAACCAGCT   960
GCTGCAGTCG GAATGGCTGG TAGTTTTACC GATGCTGAAA GAAGAAAGTG TGAAGAAGAA  1020
CTTGCTAAAT TGTATAAACA GCTTGATGAC AAGGATGAAG AGATTAACCA ACAAAGCCAA  1080
TTGGTAGAGA AATTGAAGAC ACAAATGCTG GATCAGGAAG AGCTTCTGGC ATCAACCAGA  1140
AGGGATCAAG ATAATATGCA AGCTGAACTG AATCGCCTCC AAGCAGAAAA TGATGCTTCT  1200
AAAGAAGAAG TCAAAGAAGT TTTACAGGCC TTAGAGGAAC TGGCTGTTAA TTATGATCAG  1260
AAGTCTCAGG AAGTTGAAGA CAAAACAAAG GAATATGAAT TGCTTAGTGA TGAATTGAAT  1320
CAAAAATCTG CAACTTTAGC AAGTATTGAT GCTGAGCTTC AGAAGCTGAA GGAAATGACC  1380
AACCACCAGA AGAAACGAGC AGCTGAAATG ATGGCATCAT TATTAAAAGA CCTTGCAGAA  1440
ATAGGAATTG CTGTGGGGAA TAACGATGTG AAGCAACCAG AAGGAACTGG TATGATAGAT  1500
GAAGAGTTTA CTGTTGCAAG ACTCTACATT AGCAAAAATGA AATCAGAAGT AAAGACCATG  1560
```

FIG. 12C

```
GTGAAACGCT GCAAACAGCT AGAAAGCACG CAGACTGAGA GCAACAAAAA AATGGAAGAA 1620
AATGAGAAAG AGTTAGCAGC ATGCCAGCTT CGGATCTCCC AACATGAAGC CAAAATCAAG 1680
TCACTGACTG AGTACCTTCA GAATGTAGAA CAAAAGAAGA GGCAGCTGGA GGAATCTGTT 1740
GATTCCCTTG GTGAGGAGCT AGTCCAACTC CGAGCACAAG AGAAAGTCCA TGAAATGGAA 1800
AAAGAGCACT TGAACAAGGT TCAGACTGCA AATGAAGTCA AGCAAGCTGT TGAGCAGCAG 1860
ATCCAGAGTC ACAGAGAAAC CCACCAAAAA CAAATCAGTA GCTTGCGAGA TGAAGTTGAG 1920
GCAAAGGAAA AGCTAATCAC TGACCTCCAA GACCAAAACC AGAAGATGGT GTTGGAGCAG 1980
GAACGGCTAA GGGTGGAGCA TGAGAGGCTG AAGGCTACAG ACCAAGAGAA GAGCAGGAAG 2040
CTGCATGAGC TCACGGTTAT GCAAGACAGA CGAGAACAAG CAAGACAAGA CTTGAAGGGT 2100
TTGGAGGAGA CCGTGGCAAA AGAACTTCAG ACTTTACACA ACCTGCGTAA GCTCTTTGTT 2160
CAGGACTTGG CTACCAGGGT GAAAAAGAGG CCGAGGTCGA CTCTGACGAC ACTGGCGGCA 2200
GTGCTGCACA GAAGCAGAAA ATCTCCTTCC TTGAAAACAA CCTTGAACAG CTCACCAAAG 2280
TGCACAAGCA GTTGGTACGT GATAATGCAG ATCTTCGCTG TGAGCTTCCT AAGTTAGAGA 2340
AACGGCTTAG AGCTACTGCA GAAAGAGTGA AAGCTTTGGA GTCAGCCCG             2389
```

Act D
[μg/mL]

Camptothecin
[μg/mL]

Colchicine
[μg/mL]

Adriamycin
[μg/mL]

Etoposide
[μg/mL]

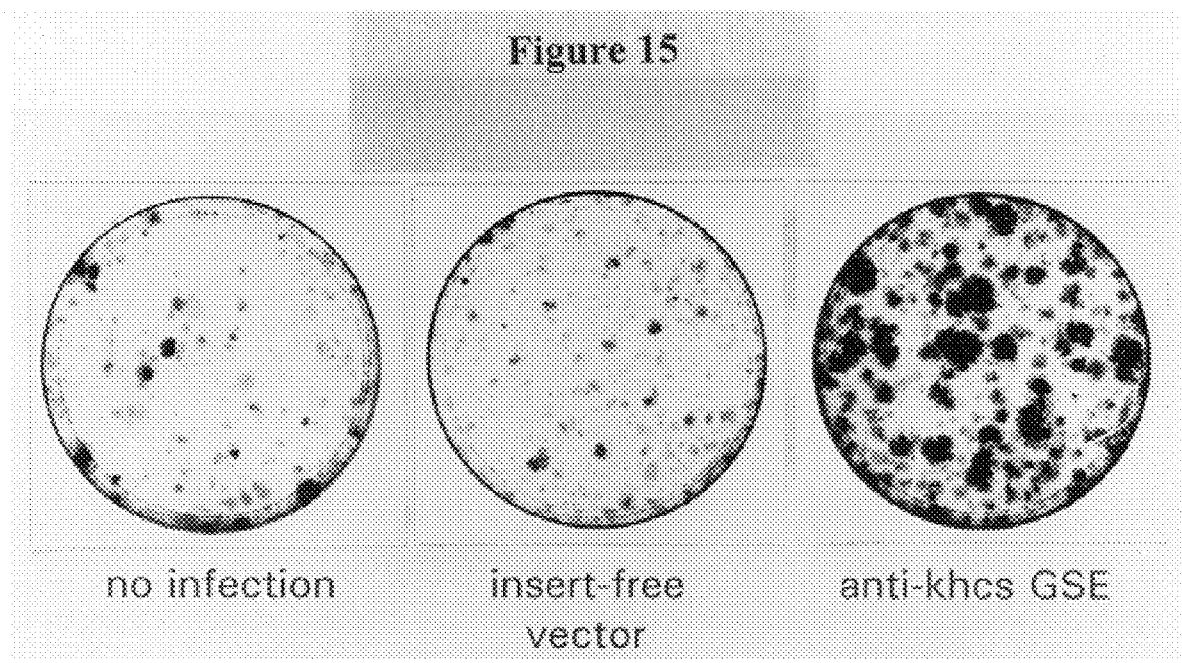

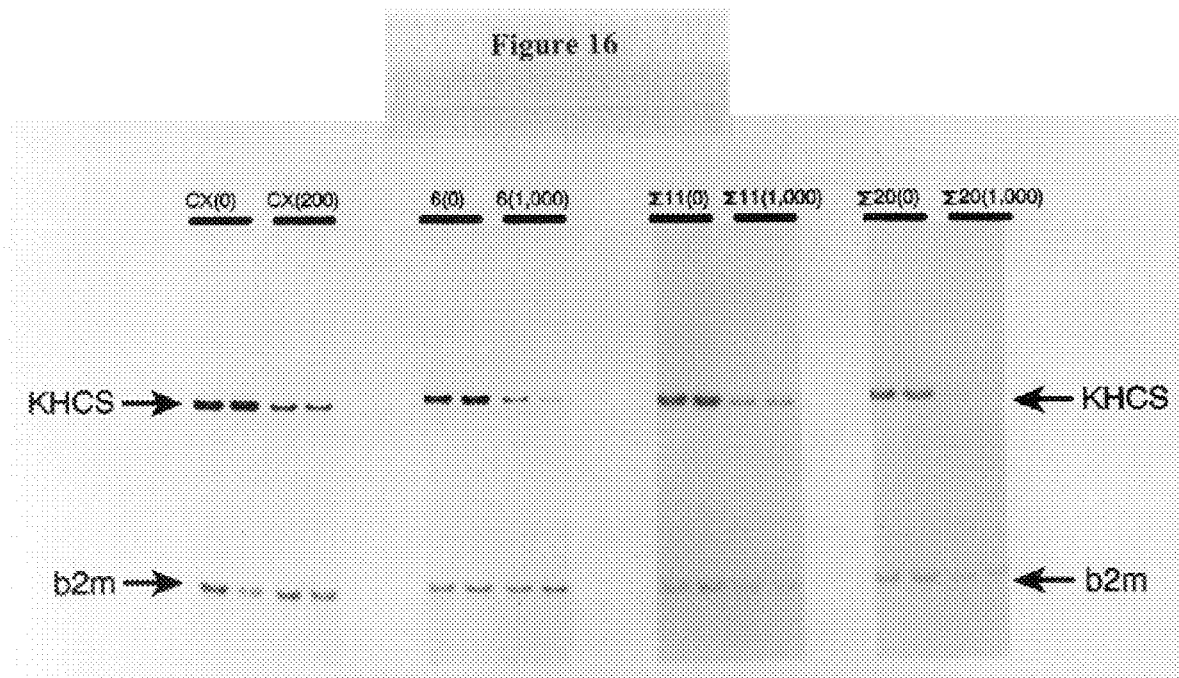

GENES AND GENETIC ELEMENTS ASSOCIATED WITH SENSITIVITY TO CHEMOTHERAPEUTIC DRUGS

This application is a divisional of U.S. Ser. No. 08/480,552, filed Jun. 7, 1995, now U.S. Pat. No. 5,665,550, issued Sep. 9, 1997, which is a continuation of U.S. Ser. No. 08/033,086, filed Mar. 9, 1993, now abandoned, which is a continuation-in-part of U.S. Ser. No. 08/039,385 [international application PCT/US91/07492, filed as international application on Oct. 11, 1991], which is a continuation-in-part of U.S. Ser. No. 07/599,730, filed Oct. 19, 1990, now U.S. Pat. No. 5,217,889, issued Jun. 8, 1993.

This invention was made with government support under grants CA39365 and CA-56738 by the National Institutes of Health. The government has certain rights in the invention.

BACKGROUND OF THE INVENTION

1. Field of the Invention

The invention relates to genetic factors associated with sensitivity to chemotherapeutic drugs. More particularly, the invention relates to methods for identifying such factors as well as to uses for such factors.

2. Summary of the Related Art

A broad variety of chemotherapeutic agents are used in the treatment of human cancer. For example the textbook *CANCER: Principles & Practice Of Oncology*, 2d Edition, (De Vita et al., Eds.), J. B. Lippincott company, Philadelphia, Pa. (1985) discloses as major antineoplastic agents the plant alkaloids vincristine, vinblastine, vindesine, and VM-26; the antibiotics actinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busufan, CCNU, MeCCNU, BCNU, streptozotocin, chlorambucil, cis-diamminedichloroplatinum, azetidinylbenzoquinone; and the miscellaneous agents dacarbazine, mAMSA and mitoxantrone.

These and other chemotherapeutic agents such as etoposide and amsacrine have proven to be very useful in the treatment of cancer. Unfortunately, some tumor cells become resistant to specific chemotherapeutic agents, in some instances even to multiple chemotherapeutic agents. Such drug resistance or multiple drug resistance can theoretically arise from either the presence of genetic factors that confer resistance to the drugs, or from the absence of genetic factors that confer sensitivity to the drugs. The former type of factors have been identified, and include the multiple drug resistance gene mdr-1 (see Chen et al., Cell 47:381–389 (1986)). However, the latter type of factor remains largely unknown, perhaps in part because such absence of factors would tent to be a recessive trait.

Identification of genes associated with sensitivity to chemotherapeutic agents is desirable, because the discovery of such genes can lead to both diagnostic and therapeutic approaches for cancer cells and for drug resistant cancer cells, as well as to improvements in gene therapy and rational drug design. Recently, some developments have been made in the difficult area of isolating recessive genetic elements, including one involved in cytotoxic drug sensitivity. Roninson et al, U.S. Pat. No. 5,217,889 (Ser. No. 07/599,730 issued Jun. 8, 1993) teaches generalized method for obtaining genetic suppressor elements (GSEs), which are dominant negative factors that confer the recessive-type phenotype for the gene to which the particular GSE corresponds. (See also Holzmayer et al., Nucleic Acids Res. 20:711–717 (1992)). Gudkov et al., Proc. Natl. Acad. Sci. USA 90:3231–3235 (1993) teaches isolation of GSEs inducing resistance to topoisomerase II-interactive drugs from topoisomerase II cDNA. However, there remains a need for identifying yet unknown genes or genetic elements associated with sensitivity to chemotherapeutic agents, a task made more difficult by the unavailability of a cloned gene as starting material for preparing GSEs. Preferably, such genes or genetic elements will be involved in a common pathway that is implicated in sensitivity to more than one chemotherapeutic agent. Most preferably, such genes or genetic elements will be identified by direct selection of GSEs causing loss of the drug sensitivity phenotype.

BRIEF SUMMARY OF THE INVENTION

The invention provides genetic suppressor elements (GSEs) that confer upon cells resistance to chemotherapeutic drugs. These GSEs are random fragments derived from genes associated with sensitivity to chemotherapeutic drugs, although the nature of such genes can be quite surprising.

In a first aspect, the invention provides a method for identifying GSEs that confer resistance to any chemotherapeutic drug for which resistance is possible. This method utilizes chemotherapeutic drug selection of cells that harbor clones from a random fragment expression library derived from total cDNA and subsequent rescue of library inserts from drug-resistance cells. In a second aspect, the invention provides a method for identifying and cloning genes that are associated with sensitivity to chemotherapeutic drugs, including genes that have not been previously discovered. This method comprises the steps of screening a full length cDNA library with a GSE that confers upon cells resistance to chemotherapeutic (or an oligonucleotide or polynucleotide constituting a portion of such a GSE) and determining the nucleotide sequence of the cDNA insert of any positive clones obtained. In a third aspect, the invention provides a method for obtaining GSEs having optimized suppressor activity for a gene associated with sensitivity to a chemotherapeutic drug. This method utilized chemotherapeutic drug selection of cells that harbor clones from a random fragment expression library derived from DNA of a gene associated with sensitivity to the same chemotherapeutic drug, and subsequent rescue of the library inserts from drug resistant cells. In a fourth aspect, the invention provides synthetic peptides and oligonucleotides that confer upon cells resistance to chemotherapeutic drugs. These synthetic peptides and oligonucleotides are designed based upon the sequence of a drug-resistance conferring GSEs according to the invention.

In a fifth aspect, the invention provides a diagnostic assay for tumor cells that are resistant to one or more chemotherapeutic drug due to the absence of expression or underexpression of a particular gene. This diagnostic assay comprises quantitating the level of expression of the particular gene product by a particular tumor cell sample to be tested. In a sixth aspect, the invention provides dominant selectable markers that are useful in gene co-transfer studies. These dominant selectable markers are drug resistance-conferring GSEs according to the invention operably linked to appropriate transcriptional control elements. In a seventh aspect, the invention provides in vivo-selectable markers that are useful both for gene therapy and for enhanced chemotherapy for cancer. Such in vivo selectable markers are transferred into blood progenitor cells, which are then used to repopulate the patient's blood exclusively with cells that contain a co-transferred therapeutic gene, or for chemotherapy, just the chemotherapeutic drug resistance conferring GSE. In a eighth aspect, the invention provides a starting point for the rational design of pharmaceutical products that are useful against tumor cells that are resistant to chemotherapeutic drugs. By examining the structure, function, localization and pattern of expression of genes associated with sensitivity to chemotherapeutic drugs, strategies can be developed for creating pharmaceutical products that will overcome drug resistance in tumor cells in which such genes are either not expressed or underexpressed.

BRIEF DESCRIPTION OF THE DRAWINGS

FIGS. 1A through 1L show the nucleotide sequences of twelve GSEs that confer etoposide resistance upon cells and that were derived from topoisomerase II DNA, using a single gene random fragment expression library, as described in Example 1. The GSEs shown are FIG. 1A clone 2V [SEQ. ID. NO. 1], FIG. 1B clone Σ11 [SEQ. ID. NO. 2], FIG. 1C clone 6 [SEQ. ID. NO. 3, FIG. 1D clone 5 [SEQ. ID. NO. 4], FIG.1E clone Σ28 [SEQ. ID. NO. 5], FIG. 1F clone Σ2 [SEQ. ID. NO. 6], FIG. 1G clone Σ20 [SEQ. ID. NO. 7], FIG. 1H clone 39 [SEQ. ID. NO. 8], FIG. 1I clone 12S [SEQ. ID. NO. 9], FIG. 1J clone Σ8 [SEQ. ID. NO. 10], FIG. 1K clone ΣVPs2 [SEQ. ID. NO. 11], and FIG. 1L clone ΣVM [SEQ. ID. NO. 12].

FIG. 2A shows the overall construction scheme. FIG. 2B shows normalization of the cDNA fragments. In FIG. 2B, t represents total unfractionated cDNA, s and d represent the single-stranded and double-stranded fractions separated by hydroxyapatite, time points indicate the period of reannealing, and tubulin, c-myc, and c-fos indicate the probes used in Southern hybridization with the total, single-stranded and double-stranded fractions.

FIGS. 5A and 5B shows etoposide resistance conferred by preselected virus (FIG. 5A) and PCR analysis of the selected and unselected populations (FIG. 5B).

FIGS. 7A and 7B demonstrates resistance to 350 ng/ml etoposide, conferred upon the cells by the GSEs VPA (FIG. 7A) and VP9-11 (FIG. 7B).

FIG. 9 shown the nucleotide sequence of the GSE anti-khcs [SEQ. ID. NO. 15].

FIG. 10 shows the nucleotide sequence of the GSE VPA [SEQ. ID. NO. 16].

FIG. 11 shown the nucleotide sequence of the GSE VP9-11 [SEQ. ID. NO. 17].

FIGS. 12A through 12C shows the nucleotide sequence of the most of the coding region of the mouse khcs cDNA [SEQ. ID. NO. 18].

FIG. 15 demonstrates increased immortalization of primary mouse embryo fibroblasts by infection with the LNCX vector containing the anti-khcs GSE, relative to cells infected with the LNCX vector alone or uninfected (control) cells.

FIG. 16 shown cDNA-PCR quantitative analysis of expression of the human khcs gene in various unselected and etoposide-selected human HeLa cells. Lanes a shows results for clone CX(O), lands a' for clone CX(200), lanes b for clone Σ11(O), lanes b' for clone Σ11 (1000), lanes c for clone 6(O), lanes c' for clone 6(1000), lanes d for clone Σ20(O) and lanes d' for clone Σ20 (1000). The numbers in parentheses for each clone name indicate the concentration of etoposide (ng/ml) present in the growth media. Bands indicative of khcs expression are shown along with bands for β-2 microglobulin expression as an internal control.

DETAILED DESCRIPTION OF THE PREFERRED EMBODIMENTS

Figure 2A:
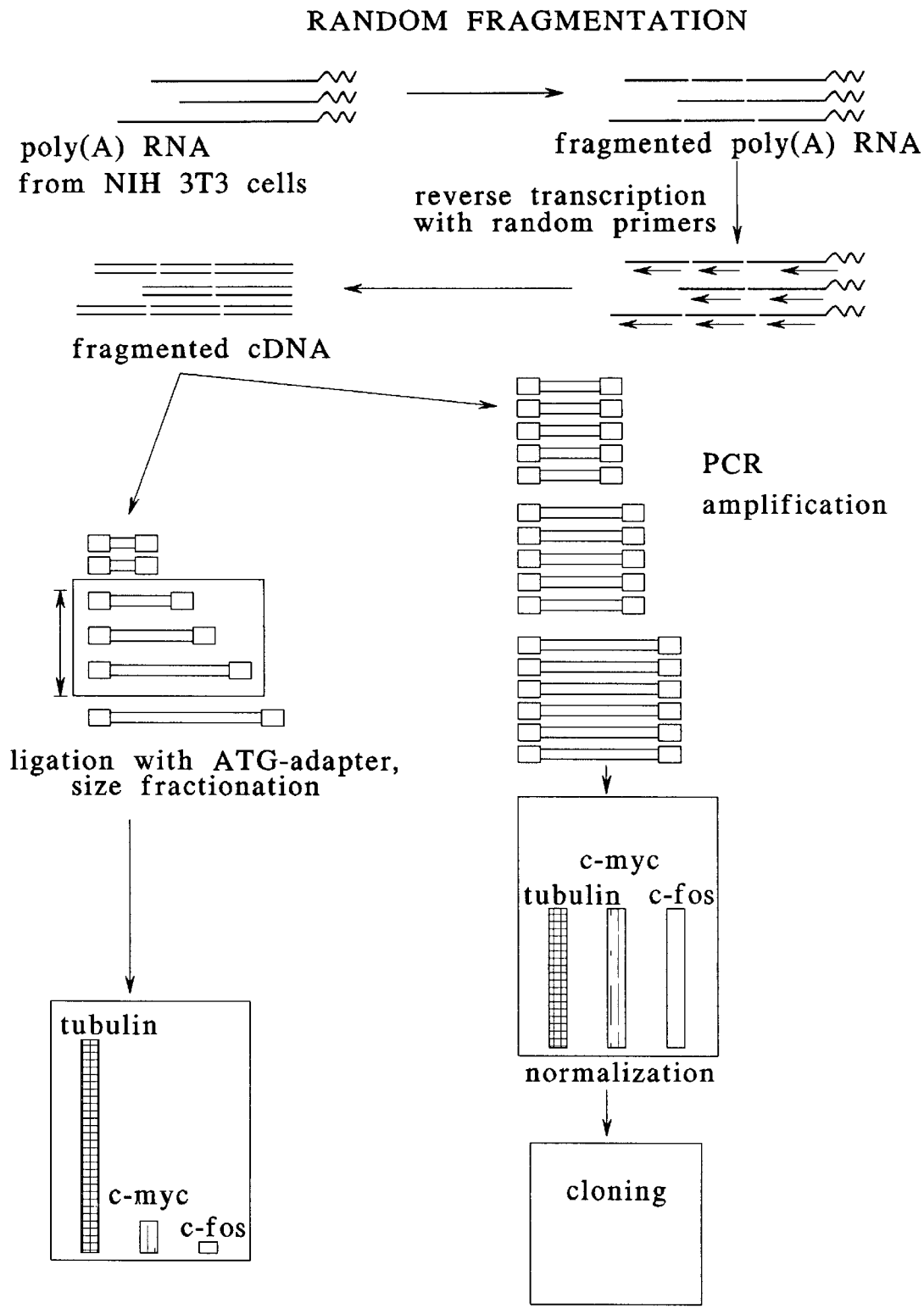
FIGS. 2A and 2B shows a scheme for construction of RFEL from NIH 3T3 cDNA.

The invention relates to means for suppressing specific gene functions that are associated with sensitivity to chemotherapeutic drugs. The invention provides genetic suppressor elements (GSEs) that have such suppressive effect and thus confer resistance to chemotherapeutic drugs. The invention further provides methods for identifying such GSEs, as well as methods for their use.

In a first aspect, the invention provides a method for identifying GSEs that confer resistance to any chemotherapeutic drug for which resistance is possible. The GSEs identified by this method will be homologous to a gene that is associated with sensitivity to one or more chemotherapeutic drug. For purposes of the invention, the term "homologous to a gene" has two different meanings, depending on whether the GSE acts through an antisense or antigene mechanism, or rather through a mechanism of interference at the protein level. In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene.

The method according to this aspect of the invention comprises the step of screening a total cDNA or genomic DNA random fragment expression library phenotypically to identify clones that confer resistance to a chemotherapeutic drug. Preferably, the library of random fragments of total cDNA or genomic DNA is cloned into a retroviral expression vector. In this preferred embodiment, retrovirus particles containing the library are used to infect cells and the infected cells are tested for their ability to survive in a concentration of a chemotherapeutic drug that kills uninfected cells. Preferably, the inserts in the library will range in size from about 100 b.p. to about 700 b.p. and more preferably, from about 200 b.p. to about 500 b.p. Most preferably, the random fragment library will be a normalized library containing roughly equal numbers of clones corresponding to each gene expressed in the cell type from which it was made, without regard for the level of expression of any gene. However, normalization of the library is unnecessary for the isolation of GSEs that are homologous to abundantly or moderately expressed genes. Once a clonal population of cells that are resistant to the chemotherapeutic drug has been isolated, the library clone encoding the GSE is rescued from the cells. At this stage, the insert of the expression library may be tested for its nucleotide sequence. Alternatively, the rescued library clone may be further tested for its ability to confer resistance to chemotherapeutic drugs in additional transfection or infection and selection assays, prior to nucleotide sequence determination. Determination of the nucleotide sequence, of course, results in the identification of the GSE. This method is further illustrated in Examples 2–5.

In a second aspect, the invention provides a method for identifying and cloning genes that are associated with sensitivity to chemotherapeutic drugs, including genes that have not been previously discovered. This is because GSEs, or portions thereof, can be used as probes to screen full length cDNA or genomic libraries to identify their gene of origin. In some cases, genes that are associated with sensitivity to chemotherapeutic drugs will turn out to be quite surprising. For example, GSEs that abrogate etoposide sensitivity are of a particularly surprising nature. The target for etoposide is topoisomerase II, a DNA unwinding enzyme. GSEs prepared from random fragments of topoisomerase II DNA do confer resistance to etoposide. Accordingly, it would be expected that most GSEs conferring etoposide resistance would be derived from DNA encoding toposisomerase II. Surprisingly, this is not the case at all. Of three etoposide resistance-conferring GSEs obtained, two were derived from previously unidentified DNA sequences. A third such GSE was derived from the kinesin heavy chain gene. Prior to this discovery, there was no suspicion that kinesin was in any way implicated in etoposide sensitivity. These results suggest that the method according to this aspect of the invention will provide much new and surprising information about the genetic basis for resistance to chemotherapeutic drugs. In addition, a kinesin-derived GSE conferring resistance to etoposide caused cellular effects suggesting that kinesin may be involved in programmed cell death. If this is indeed the case, then the method according to this aspect of the invention also provides valuable information about the genetic basis for senescence and cell death. This may have important implications for studying genes involved in development, since GSEs used to identify genes associated with chemotherapeutic drug resistance or senescence can also be expressed as transgenes in embryos to determine the role of such genes in development. The method according to this aspect of the invention and its use for studying genes identified thereby and their cellular effects are further illustrated in Example 6–8.

In a third aspect, the invention provides a method for obtaining GSEs having optimized suppressor activity for a gene associated with sensitivity to a chemotherapeutic drug. In the method according to this aspect of the invention, an initial GSE is obtained by the method according to the first aspect of the invention. Then, the gene from which the GSE is derived is identified and cloned by the method according to the second aspect of the invention. This gene is then randomly fragmented and cloned into an expression vector, preferably a retroviral vector, to obtain a random fragment expression library derived exclusively from the gene of interest. This library is then transferred to and expressed in mammalian cells, which are selected in the presence of the appropriate chemotherapeutic drug. As a practical matter, such a library will contain a much greater variety of GSEs derived from the gene of interest than will a random fragment library prepared from total cDNA. Consequently, the likelihood of obtaining optimized GSEs, as determined by maximized chemotherapeutic drug resistance, from the single gene random fragment library is much higher. A single gene random fragment library approach is shown in greater detail in Example 1.

In a fourth aspect, the invention provides synthetic peptides and oligonucleotides that are capable of inhibiting the function of genes associated with sensitivity to chemotherapeutic drugs. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE is discovered and sequenced, and its orientation is determined, it is straightforward to prepare an oligonucleotide corresponding to the nucleotide sequence of the GSE (for antisense-oriented GSEs) or amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that may independent GSE clones corresponding to a particular gene will have the same 5' or 3' terminus, but generally not both. This suggests that many GSEs have one critical endpoint, from which a simple walking experiment will determine the minimum size of peptide or oligonucleotide necessary to inhibit gene function. For peptides, functional domains as small as 6–8 amino acids have been identified for imunoglobulin binding regions. Thus, peptides or peptide mimetics having these or larger dimensions can be prepared as GSEs. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Preferably, such oligonucleotides will have from about 12 to about 100 nucleotides. As used herein, the term oligonucleotide includes modified oligonucleotides having nuclease-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridged methylene phosphonate and bridged phosphorothioate internucleotide linkages. The synthesis of oligonucleotides containing these modified linkages is well known in the art. (See e.g., Uhlmann and Peyman, Chemical Reviews 90:543–584 (1990); Schneider and Banner, Tetrahedron Letters 31:335 (1990). The term oligonucleotides also includes oligonucleotides having modified bases or modified ribose or deoxyribose sugars.

In a fifth aspect, the invention provides a diagnostic assay for tumor cells that are resistant to one or more chemotherapeutic drug due to absence of expression or underexpression of a particular gene. By using the methods according to the first and second aspects of the invention such a gene will be identified and cloned. To determine whether absence of expression or underexpression of such a gene is a naturally occurring, and thus medically significant basis for chemotherapeutic drug resistance, human tumor cells can be treated with cytotoxic quantities of an appropriate chemotherapeutic drug to select for spontaneous drug resistant mutants. These mutants can then be assessed for their level of expression of the particular gene of interest. Absence of expression or significantly reduced expression indicates a natural mechanism of chemotherapeutic drug resistance. Accordingly, such reduced or absent expression can be the basis for a diagnostic assay for tumor cell resistance to the chemotherapeutic drug or drugs of interest. A first embodiment of a diagnostic assay according to this aspect of the invention utilizes an oligonucleotide or oligonucleotides that is/are homologous to the sequence of the gene for which expression is to be measured. In this embodiment, RNA is extracted from a tumor sample, and RNA specific for the gene of interest is quantitated by standard filter hybridization procedures, an RNase protection assay, or by quantitative cDNA-PCR. (See Noonan et al, Proc. Natl. Acad. Sci. USA 87:7160–7164 (1990)). In a second embodiment of a diagnostic assay according to this aspect of the invention, antibodies are raised against a synthetic peptide having an amino acid sequence that is identical to a portion of the protein that is encoded by the gene of interest. These antibodies are then used in a conventional quantitative immunoassay (e.g., RIA or immunohistochemical assays) to determine the amount of the gene product of interest present in a sample of proteins extracted from the tumor cells to be tested, or on the surface or at locations within the tumor cells to be tested.

In a sixth aspect, the invention provides dominant selectable markers that are useful in gene co-transfer studies. Since GSEs according to the invention confer resistance to chemotherapeutic drugs, the presence of a vector that expresses the GSE can readily be selected by growth of a vector-transfected cell in a concentration of the appropriate cytotoxic drug that would by cytotoxic in the absence of the GSE. GSEs according to the invention are particularly well suited as dominant selectable markers because their small size allows them to be easily incorporated along with a gene to be cotranfered even into viral vectors having limited packaging capacity.

In a seventh aspect, the invention provides in vivo-selectable markers that are useful both in gene therapy and in enhancing the effectiveness of chemotherapy. For gene therapy, GSEs according to the invention can be co-transferred on a vector into human $CD34^+$ blood progenitor cells from a patient along with a therapeutic gene that, when expressed, will alleviate a genetic disorder. The cells can be selected in vitro for resistance to an appropriate chemotherapeutic drug, thereby assuring successful transfer of the GSE, and by implication, of the therapeutic gene as well. The progenitor cells containing the GSE and therapeutic gene can then be returned to the patient's circulation. Finally, the cells containing the GSE and therapeutic gene can be selected in vivo by administration of the appropriate chemotherapeutic drug (to which the GSE confers resistance) in a concentration that is cytotoxic to normal blood cells. In this way, those cells having the GSE and therapeutic gene will repopulate the patient's blood.

For enhancement of chemotherapy, a GSE according to the invention can be transferred alone or with another gene on an expression vector into $CD34^+$ blood progenitor cells taken from a cancer patient. In vitro selection of the progenitor cells harboring the GSE is then carried out, using the appropriate chemotherapeutic drug. The selected cells are then returned to the patient's circulation and allowed time to begin repopulating the blood. After an appropriate period, aggressive chemotherapy can be carried out, using much higher than ordinary concentrations of an appropriate chemotherapeutic drug (to which the GSE confers resistance), since toxic side effects to the immune system will be avoided due to GSE expression in those cells.

In either of these therapeutic contexts, it may be desirable to have the GSE expressed in the progenitor cells (and subsequently in the blood cells), only when its expression is beneficial, i.e., during in vitro selection of cells harboring the GSE and again during in vivo selection or chemotherapy. To accomplish this, an inducible promoter can be used to express the GSE. Then, the appropriate inducing agent is added to the cells prior to and during in vitro selection and again prior to and during in vivo selection or chemotherapy. As long as the inducing agent is not normally present in the human body, the GSE will not be expressed at any other time.

In an eighth aspect, the invention provides a starting point for the rational design of pharmaceutical products that can counteract resistance by tumor cells to chemotherapeutic drugs. The protein sequence encoded by genes from which the GSEs were derived can be deduced from the cDNA sequence, and the function of the corresponding proteins may be determined by searching for homology with known genes or by searching for known functional motives in the protein sequence. If these assays do not indicate the protein function, it can be deduced through the phenotypic effects of the GSEs suppressing the gene. Such effects can be investigated at the cellular level, by analyzing various growth-related, morphological, biochemical or antigenic changes associated with GSE expression. The GSE effects at the organism level can also be studied by introducing the corresponding GSEs as transgenes in transgenic animals (e.g. mice) and analyzing developmental abnormalities associated with GSE expression. The gene function can also be studied by expressing the full-length cDNA of the corresponding gene, rather than a GSE, from a strong promoter in cells or transgenic animals, and studying the changes associated with overexpression of the gene.

Full-length or partial cDNA sequences can also be used to direct protein synthesis in a convenient prokaryotic or eukaryotic expression system, and the produced proteins can be used as immunogens to obtain polyclonal or monoclonal antibodies. These antibodies can be used to investigate the protein localization and as specific inhibitors of the protein function, as well as for diagnostic purposes. In particular, antibodies raised against a synthetic peptide encoded by part of the complement of the sequence of the GSE anti-khcs, or the corresponding region of the human KHCS protein should be particularly useful, as should antibodies raised against an amino acid sequence encoded by part of the VPA or VP9-11 (see FIGS. 9–11).

Understanding the biochemical function of a gene involved in drug sensitivity is likely to suggest pharmaceutical means to stimulate or mimic the function of such a gene and thus augment the cytotoxic response to anticancer drugs. For example, if the gene encodes an enzyme producing a certain compound, such a compound can be synthesized chemically and administered in combination with cytotoxic drugs. If a pharmaceutical approach is not apparent from the protein function, one may be able to upmodulate gene expression at the level of transcription. This can be done by cloning the promoter region of the corresponding gene and analyzing the promoter sequence for the presence of cis elements known to provide the response to specific biological stimulators.

The most straightforward way to increase the expression of a drug sensitivity gene, identified through the GSE approach, would be to insert a full-length cDNA for such a gene into a retroviral vector. Such a vector, in the form of a recombinant retrovirus, will be delivered to tumor cells in vivo, and, upon integration, would sensitize such cells to the effects of the corresponding chemotherapeutic drug. A similar strategy for selective delivery of a drug-sensitivity gene into rat brain tumors, followed by curative treatment with the appropriate drug, was reported by Culver et al., Science 256:1550–1552 (1992). The selective delivery to tumor cells can be accomplished on the basis of the selectivity of retrovirus-mediated transduction for diving cells. Alternatively, the selectivity can be achieved by driving the expression of the drug sensitivity gene from a tissue- or tumor-specific promoter, such as, for example, the promoter of the carcinoembryonic antigen gene.

The protein structure deduced from the cDNA sequence can also be used for computer-assisted drug design, to develop new drugs that affect this protein in the same manner as the known anticancer drugs. The purified protein, produced in a convenient expression system, can also be used as the critical component of in vitro biochemical screening systems for new compounds with anticancer activity. Accordingly, mammalian cells that express chemotherapeutic drug resistance-conferring GSEs according to the invention are useful for screening compounds for the ability to overcome drug resistance.

The following examples are intended to further illustrate certain preferred embodiments of the invention and are not limiting in nature.

EXAMPLE 1

Development of GSEs for Human Topoisomerase II

Topoisomerase II is a DNA unwinding enzyme that serves as a target for many anti-cancer drugs, including etoposide, doxorubicin and amsacrine. The enzyme normally acts by double-strand DNA cleavage, followed by strand passage and religation of the breaks. Anti-cancer drugs cause trapping of the enzyme in complexes having double-strand breaks held together by the enzyme, thereby leading to lethal damage in replicating cells. Some cell lines that are resistant to anti-cancer drugs that interact with topoisomerase II have decrease expression of this enzyme.

Random fragment selection of GSEs requires transfer of the expression library into a very large number of recipient cells. Therefore, to prepare a random fragment library containing GSEs for topoisomerase II, the efficient retroviral vector system was chosen. Overlapping cDNA clones spanning the entire coding sequence for topoisomerase II were mixed and randomly fragmented into 250–350 bp fragments by DNase I in the presence of $Mn^{++}$ ions and fragment termini were filled in with T4 DNA polymerase and Klenow fragment of DNA polymerase I. After ligation with a synthetic adaptor providing translation initiation and termination codons, the fragment mixture was amplified by PCR, using adaptor-derived primers. The amplified mixture was cloned into the LNCX retroviral vector which contains a neo gene. (see Miller and Rosman, Biotechniques 7:980–986 (1989)).

A random fragment library containing 20,000 independent clones was obtained, and was used to transfect amphotropic and ecotropic virus-packaging cell lines derived from NIH 3T3 cells, to effect ping-pong replication-mediated amplification of the virus (e.g., see Bodine, et al. Proc. Nalt. Acad. Sci. USA 87:3738–3742 (1990)). This resulted in a random fragment expression library (RFEL), a set of recombinant retroviruses containing a representative mixture of inserts derived from topoisomerase II gene sequences.

The uniformity of sequence representation in RFEL was monitored as follows. NIH 3T3 cells were infected with virus-containing supernatant, followed 24 hours later by PCR amplification of integrated proviral insert sequences in the presence of $[^{32}P]$ alpha-dNTP. An aliquot of the PCR-amplified mixture was subjected to gel electrophoresis to establish the absence of predominant bands. Another aliquot was used as a probe for a Southern bolt to topoisomerase II cDNA digested with several frequently cutting restriction enzymes. A representative sequence mixture was obtained, as evidenced by the absence of a predominant band in the first test, and uniform hybridization to all fragments in the second test.

RFEL was then used to infect HeLa cells, and the infectants were selected with G418. Colonies of G418-resistant cells, having about 50–70 cells each, were then exposed to etoposide at a concentration of 200 μg/ml. Approximately 50 of 10,000 G418-resistant colonies were etoposide resistant, compared to a frequency of $<10^{-4}$ when insertless retroviruses were used as a control. Cell lines were isolated from etoposide-resistant colonies. Amphotropic and ecotropic packaging cell lines producing RFEL were also selected from etoposide resistance. Virus from etoposide resistant packaging cell lines was used to infect HeLa cells, which were then selected with G418. G418-resistant infectants were challenged with three topoisomerase II-interactive anticancer drugs: etoposide, teniposide and amsacrine. A high proportion of infected cells were resistant to all three drugs, thus demonstrating that etoposide selection of mouse packaging cell lines has led to the generation of GSEs active in both human and mouse cells. These infectants were also used to establish cell lines. RFEL-derived inserts were recovered from etoposide resistant cell lines by PCR and recloned into LNCX vector. The newly-derived clones were then individually tested for the ability to confer resistance to etoposide upon transfection into HeLa cells, to confirm the GSE activity of the corresponding inserts.

Sequence analysis of 26 different isolated clones revealed that 16 of them were inserted in antisense and 10 in sense orientation. Of the 12 GSEs confirmed, 7 were sense and 5 antisense, as shown in Table I. The sequences of the confirmed GSEs are shown in FIGS. 1A through 1L. The sense-oriented inserts of the confirmed GSEs encode 37–99 amino acid long topo II-derived peptides, initiating either from the ATG codon provided by the adaptor, or from the internal ATG codon within the open reading frame of Topoisomerase II, located close to the 5' end of the insert in an appropriate context for translation initiation. Four of the confirmed antisense GSEs come from the 3' third of the cDNA and one from the 5' end of cDNA, including the translation start site. Of the sense-oriented GSEs, five are derived from the central portion of the protein that includes the active site tyrosine-804 that covalently binds to DNA and the "leucine zipper" region involved in dimerization of Topoisomerase II. One GSE peptide is derived from the region near the N-terminus and another from the region near the C-terminus of the protein; no known functional sites are associated with either segment.

TABLE I

Confirmed Topoisomerase II-Derived GSE

| Clones | Orientation (Sense/Antisense) | Position in cDNA[a] | Position of peptide[b] |
|---|---|---|---|
| 2V | Antisense | −18–145 | |
| Σ11 | Sense | 393–605 | 134–201 |
| 6 | Sense | 2352–2532 | 808–844 |
| 5 | Sense | 2511–2734 | 846–911 |
| Σ28 | Sense | 2603–2931 | 879–977 |
| Σ2 | Antisense | 3150–3343 | |
| Σ20 | Antisense | 3486–3692 | |
| 39 | Antisense | 3935–4127 | |
| 12S | Sense | 4102–4343 | 1368–1447 |
| ΣVPs2 | Sense | 2494–2834 | 846–944 |
| Σ8 | Antisense | 4123–4342 | |
| ΣVM | Sense | 2501–2670 | 846–890 |

[a]Position in the cDNA sequence of topoisomerase II; residues numbered as in Tsai-Pflugfelder et al., Proc. Natl. Acad. Sci. USA 85:7177–7181 (1988).
[b]Position of the peptide encoded by sense-oriented GSEs in the amino acid sequence of topoisomerase II; translation assumed to initiate from the first ATG codon in the correct open reading frame.

These results demonstrate that GSEs that act according to multiple mechanisms to confer etoposide resistance can be prepared from a random fragment library of DNA encoding topoisomerase II. In addition, these results show that GSEs produced from one mammalian species can be active in another mammalian species.

EXAMPLE 2

Generation of a Normalized Random Fragment cDNA Library in a Retroviral Vector

Figure 2B:
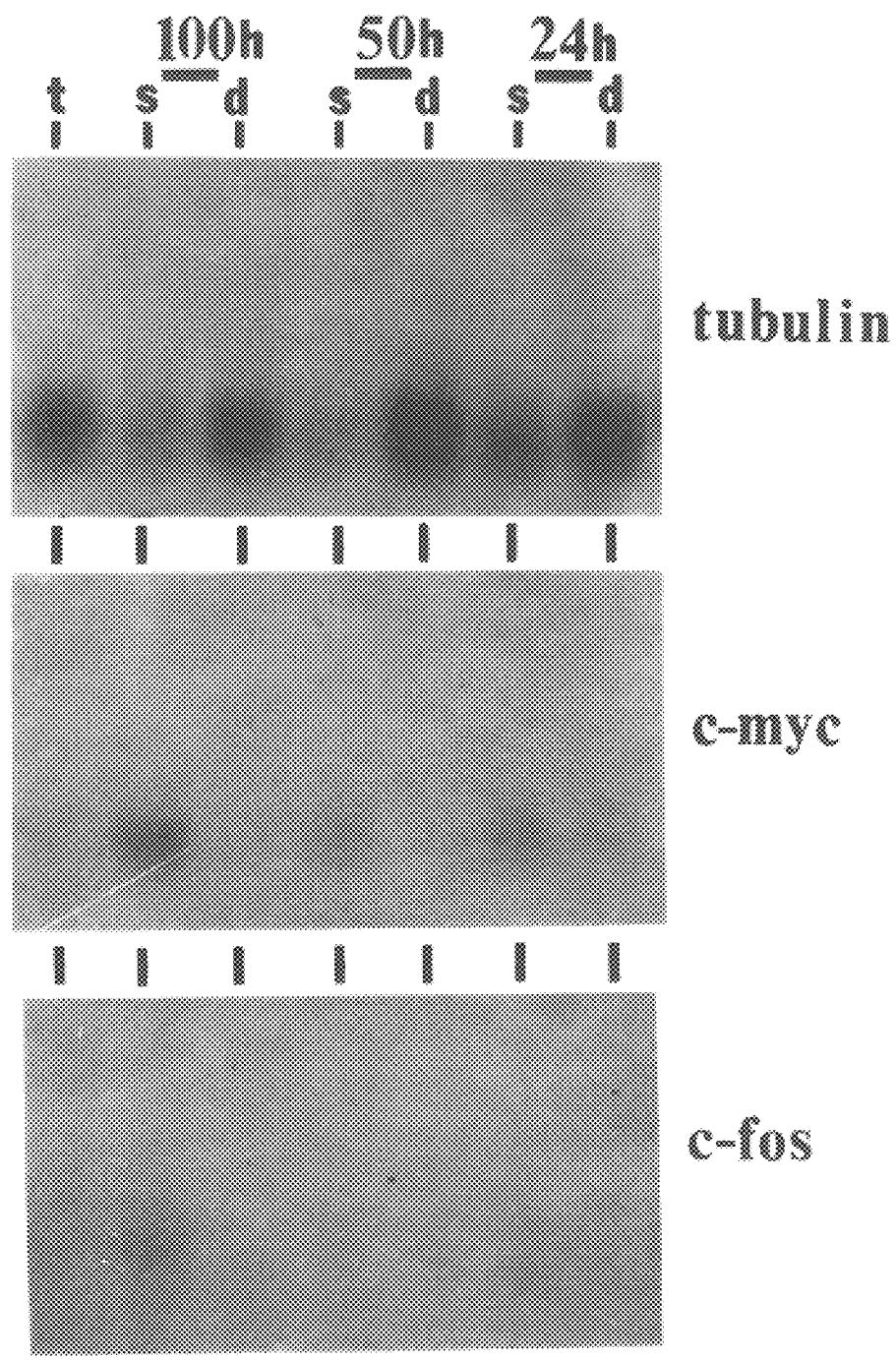

As shown in FIGS. 2A and 2B a normalized cDNA population was prepared using a modification of the protocol of Patanjali et al., Proc. Natl. Acad. Sci. USA 88:1943–1947 (1991). Poly(A)+ RNA was extracted from NIH 3T3 cells. To obtain mRNAs for different genes expressed at various stages of the cell growth, one half of the RNA was isolated from a rapidly growing culture and the other half from quiescent cells that had reached complete monolayer confluency. To avoid overrepresentation of the 5'-end sequences in a randomly primed cDNA population, RNA was fragmented by boiling to an average size range 600–1,000 nucleotides. These RNA fragments were then used for preparing randomly primed double-stranded cDNA. This randomly primed cDNA was then ligated to a synthetic adaptor providing ATG codons in all three possible reading frames and in a proper context for translation initiation. The structure of the adaptor (see FIG. 3B) determined its ligation to the blunt-ended fragments of the cDNA in such a way that each fragment started from initiation codons independently from its orientation. The adaptor was not supplied with termination codons in the opposite strand since the cloning vector pLNCX, contained such codons immediately downstream of the cloning site. This vector has been described by Miller and Rosman, Biotechniques 7:980–986 (1989). The ligated mixture was amplified by PCR, using the "sense" strand of the adaptor as a PCR primer, in contrast to the method of Patanjali et al., which utilized cloning the initial cDNA preparation into a phage vector and then using vector-derived sequences as PCR primers to amplify the cDNA population. The PCRs were carried out in 12 separate reactions that were subsequently combined, to minimize random over- or under-amplification of specific sequences and to increase the yield of the product. The PCR-amplified mixture was size-fractionated by gel electrophoresis, and 200–500 bp fragments were selected for subsequent manipulations in contrast to Patanjali's fragment size range of from 400 to 1,600 bp.

For normalization, the cDNA preparation was denatured and reannealed, using different time points, as described by Patanjali et al., supra, and shown in FIGS. 2A and 2B, for reannealing. The single-stranded and double-stranded DNAs from each reannealed mixture were separated by hydroxyapatite chromatography. The single-stranded DNA fractions from each time point of reannealing were PCR-amplified using the adaptor-derived primer and analyzed by Southern hybridization for the relative abundance of different mRNA sequences. The fraction that contained similar proportions of tubulin, c-myc and c-foc cDNA sequences (see FIGS. 2A and 2B), corresponding to high-, medium- and low-expressed genes, respectively, was used for the library preparation.

Figure 3A:
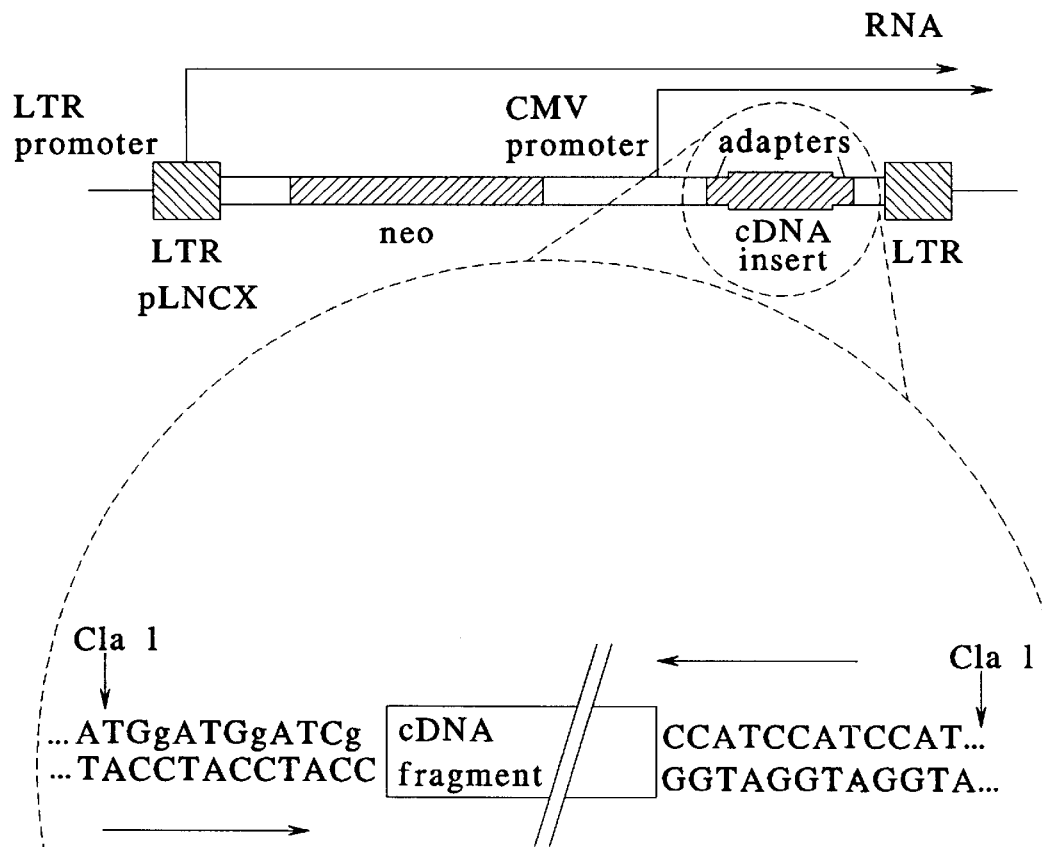
FIGS. 3A and 3B shows the structure of the LNCX vector and the adaptor used for cDNA cloning. The nucleotide sequences are shown for the ATG-sense [SEQ. ID. NO. 13] and ATG-antisense [SEQ. ID. NO. 14] strands of the adaptor.
Figure 3B:
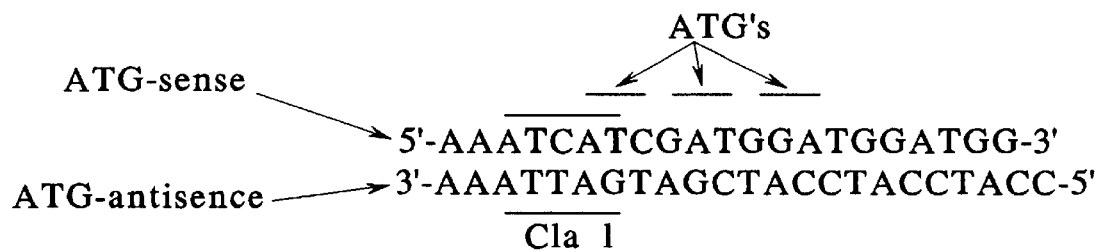

The normalized cDNA preparation was cloned into the Cla I site of the MoMLV-based retroviral vector pLNCX, which carries the neo (G418 resistance) gene, transcribed from the promoter contained in the retroviral long terminal repeat (LTR), and which expresses the inserted sequence from a strong promoter of the cytomegalovirus (CMV) (see FIG. 3A). The ligation mixture, divided into five portions, was used for five subsequent large-scale transformations of E. coli. The transformed bacteria were plated on the total of 500 agar plates (150 mm in diameter) and the plasmid population (18 mg total) was isolated from the colonies washed off the agar. A total of approximately $5 \times 10^7$ clones were obtained, more than 60% of which carried the inserts of normalized cDNA, as estimated by PCR amplification of inserts from 50 randomly picked colonies. These results demonstrate the feasibility of generating a normalized cDNA library of as many as $3 \times 10^7$ recombinant clones in a retroviral plasmid expression vector.

EXAMPLE 3

Transduction of a Retroviral Random Fragment Library into Virus-Packaging Cell Lines and NIH 3T3 Cells The plasmid library prepared according to Example 2 was converted into a mixture of retroviral particles by transfection into virus-packaging cells (derivatives of NIH 3T3) that express retroviral virion proteins. Examples of such cell lines have been described by Markowitz et al., Virology 167:400–406 (1988). Ecotropic and amphotropic virus-packaging cell lines, GP+E86 and GP+envAm12, respectively, were mixed at a 1:1 ratio, and $10^7$ cells of this mixture were transfected with the plasmid library under standard calcium phosphate coprecipitation conditions. This transfection resulted in the packaging and secretion of ecotropic and amphotropic virus particles, which rapidly spread through the packaging cell population, since ecotropic viruses are capable of infecting amphotropic packaging cells and vice versa. The yield of the virus, as measured by the number of G418-resistant colonies obtained after the infection of NIH 3T3 cells, reached $10^5$ infectious units per 1 ml of media during the stage of transient transfection (1–3days), then decreased (4–8 days) and then rapidly increased due to the expression of proviral genomes that became stably integrated in most of the packaging cells. The yield of the virus 9–12 days after transfection reached $>10^6$ per 1 ml of media supernatant. At this stage, the library showed fairly even representation of different fragments, but at later stages individual virus-producing clones began to predominate in the population, leading to uneven representation of cDNA-derived inserts. The uniformity of sequence representation in the retroviral population was monitored by rapid extraction of DNA from cells infected with the virus-containing supernatant, followed by PCR amplification of inserts. The inserts were analyzed first by the production of a continuous smear in ethidium-bromide stained agarose gel and then by Southern hybridization with different probes, including topiosomerase II, c-myc and tubulin. As long as each gene was represented by a smear of multiple fragments, the representativity of the library was considered to be satisfactory.

In other experiments, for transducing the random-fragment normalized cDNA library into NIH 3T3 cells, without loss of representativity, NIH 3T3 cells were infected either with a virus produced at the transient stage of transfection (days 1–3), or with the high-titer virus collected 10–12 days after transfection. In the latter case, 100 ml of viral suspension contained more than $10^8$ infectious units. In the case of the "transient" virus, NIH 3T3 cells were infected with at least $10^7$ recombinant retroviruses by using 500 ml of media from virus-producing cells (five rounds of infection, 100 ml of media in each). These results demonstrate the feasibility of converting a large and complex random fragment library into retroviral form and delivering it to a non-packaging cell line without loss of complexity.

EXAMPLE 4

Isolation of GSEs Conferring Resistance to the Chemotherapeutic Drug Etoposide

Figure 4:
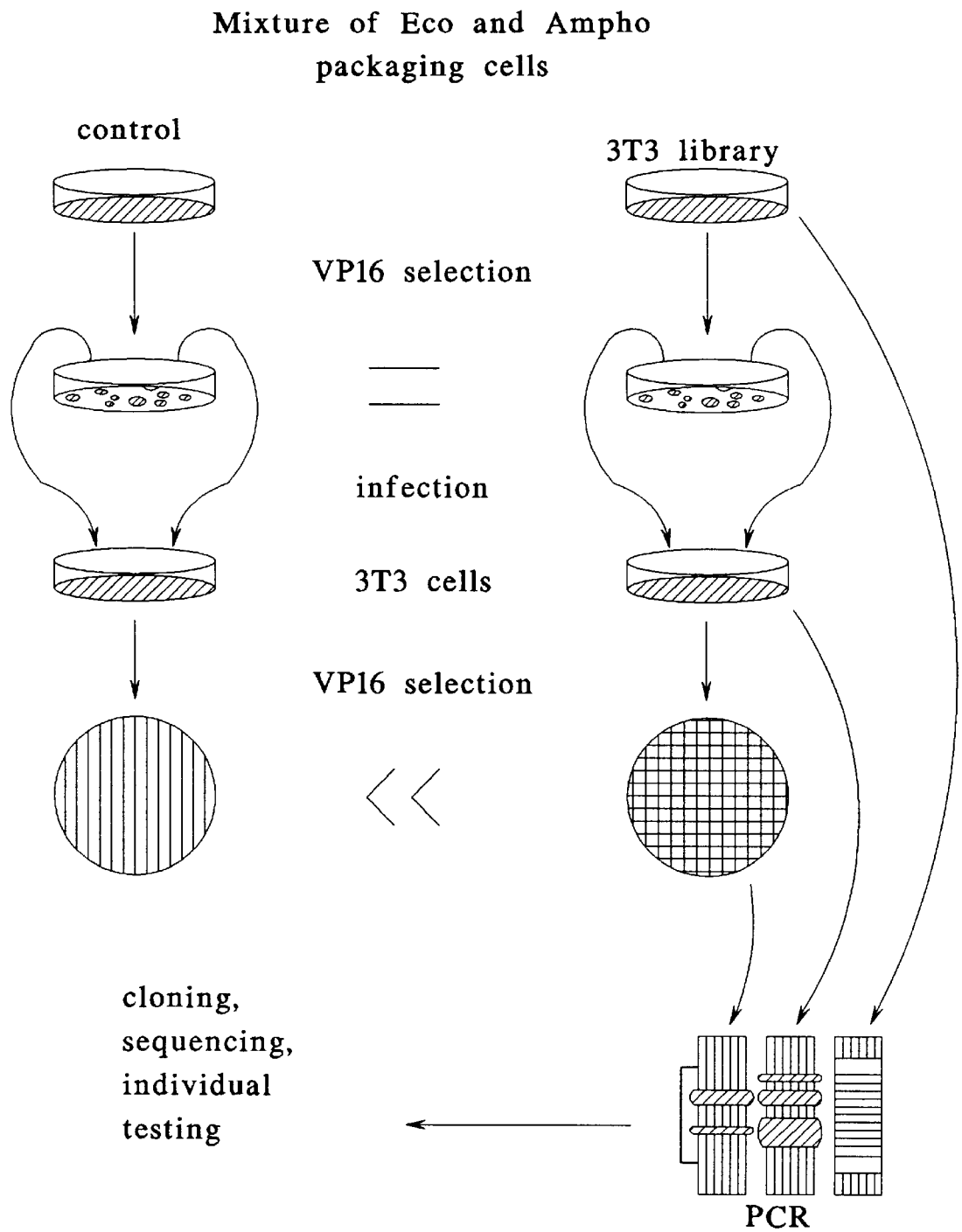
FIG. 4 shows the overall scheme for selecting cell lines containing chemotherapeutic drug resistance-conferring GSEs and rescuing the GSEs from these cells.
Figure 5B:
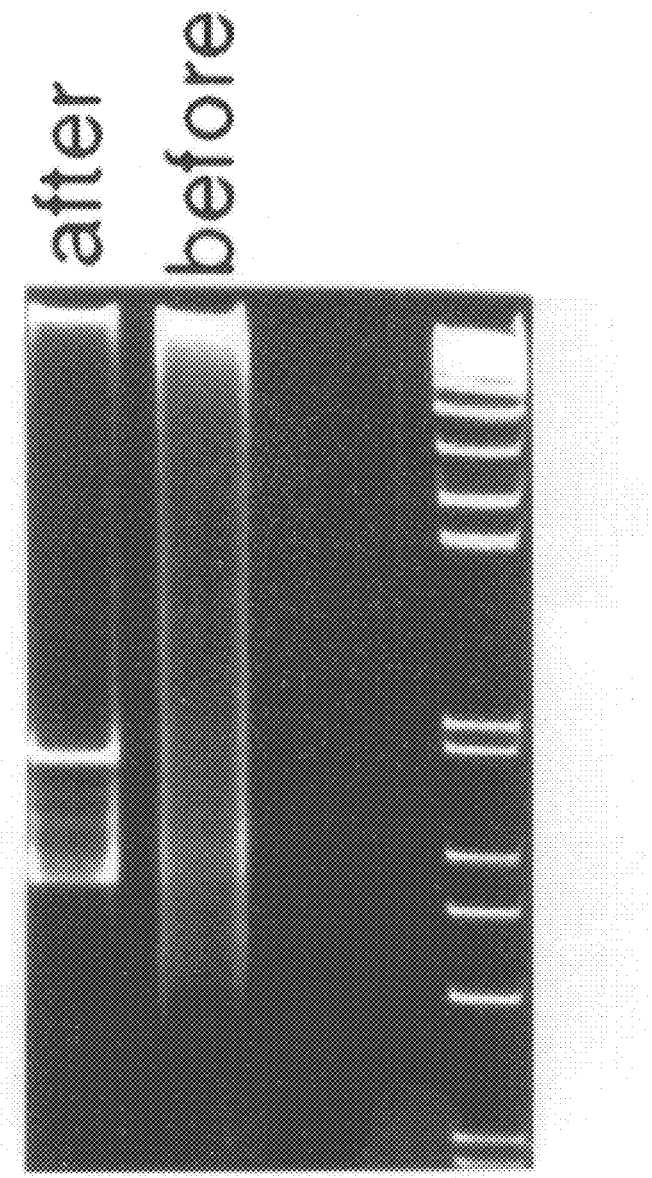

The overall scheme for the selection of GSEs conferring etoposide resistance is illustrated in FIG. 4. This selection was carried out directly on virus-producing packaging cells, in the expectation that cells whose resistant phenotype is caused by the GSE expression will produce virus particles carrying such a GSE. The mixture of amphotropic and ecotropic packaging cells was transfected with the cDNA library in the LNCX vector, prepared according to Example 2 and the virus was allowed to spread through the population for 9 days. Analysis of a small part of the population for G418 resistance showed that practically 100% of the cells carried the neo-containing provirus. The cells were then exposed to 350 ng/ml etoposide for 15 days and then allowed to grow without drug for two more weeks. No difference was observed between the numbers of colonies obtained in the experiment and in the control (uninfected cells or cells infected with the insert-free LNCX virus) after etoposide selection. The virus present in the media supernatant of the surviving cells was then used to infect NIH 3T3 cells followed by etoposide selection using essentially the same protocol. NIH 3T3 cells infected with the library-derived virus produced by packaging cells that were selected with etoposide showed a major increase in the number of etoposide-resistant cells relative to the control cells infected with the insert-free LNCX virus, indicating the presence of biologically active GSEs in the preselected virus population (see FIG. 5A).

Figure 6:
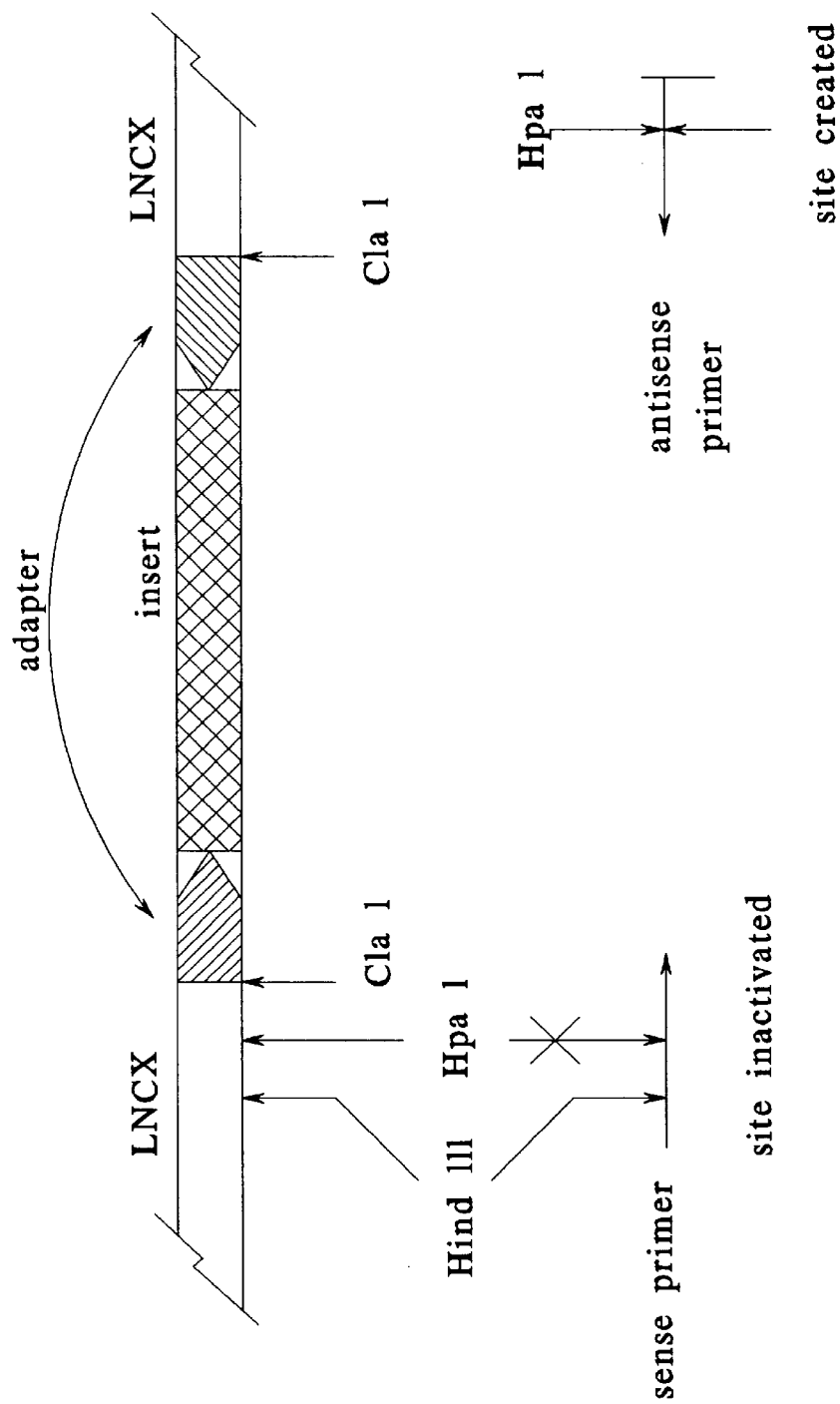
FIG. 6 shown a scheme for recloning individual PCR-amplified fragments from etoposide resistant selected cells into the LNCX vector, as described in Example 4.
Figure 7A:
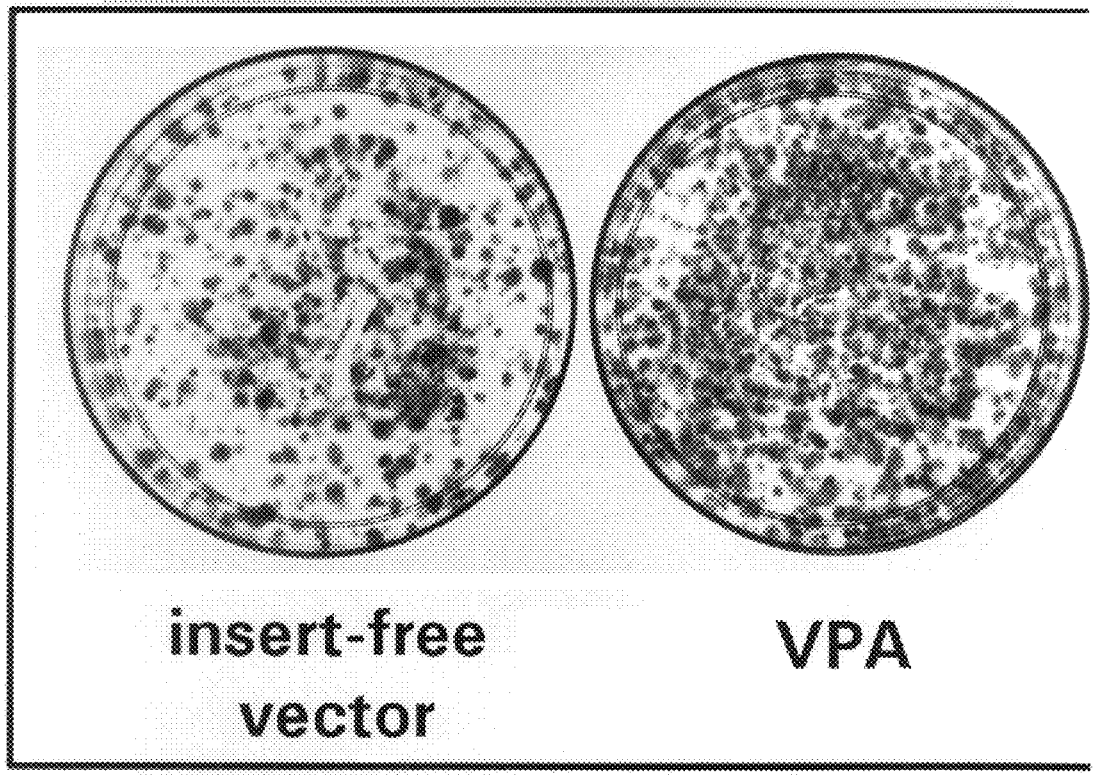
Figure 8A:
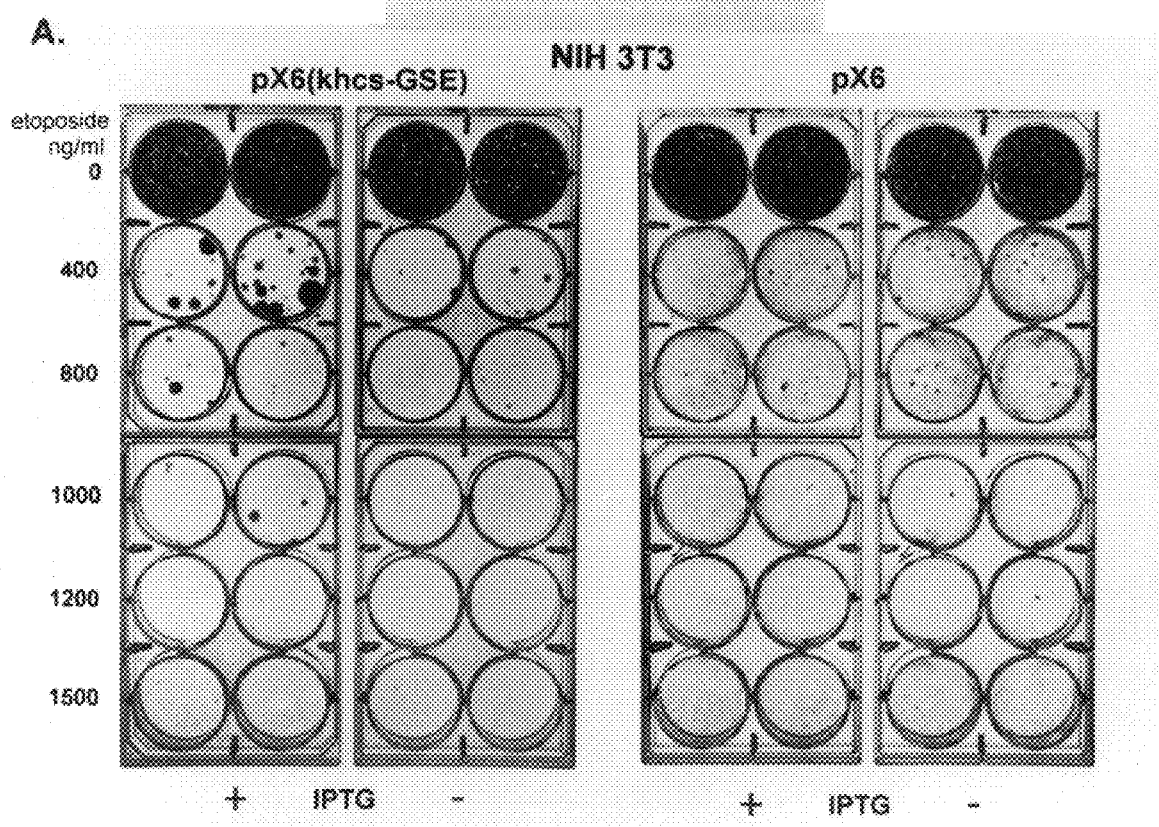
FIGS. 8A and 8B shows resistance to various concentrations of etoposide, conferred upon the cells by the GSE anti-khcs under an IPTG-inducible promoter (FIG. 8A) and the scheme for this selection (FIG. 8B).
Figure 8B:
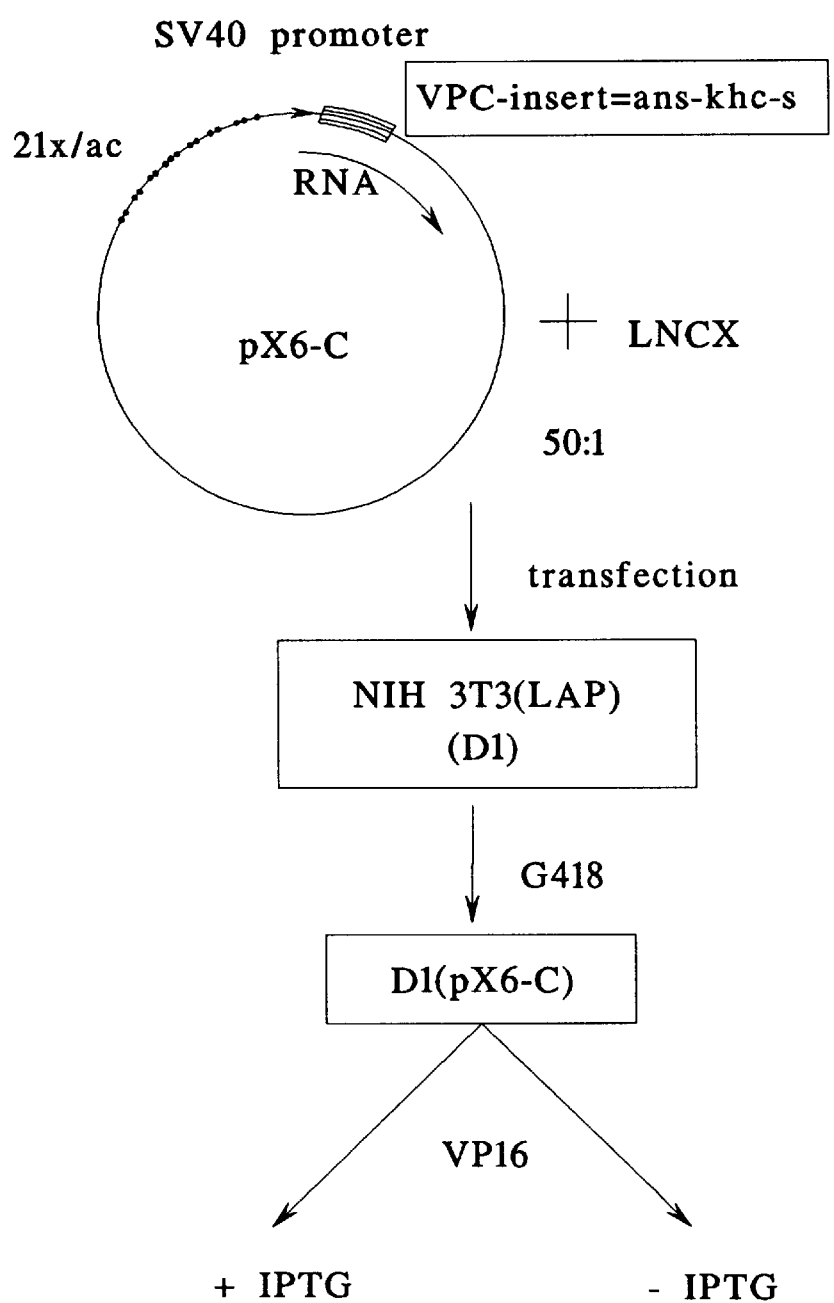
Figure 13A:
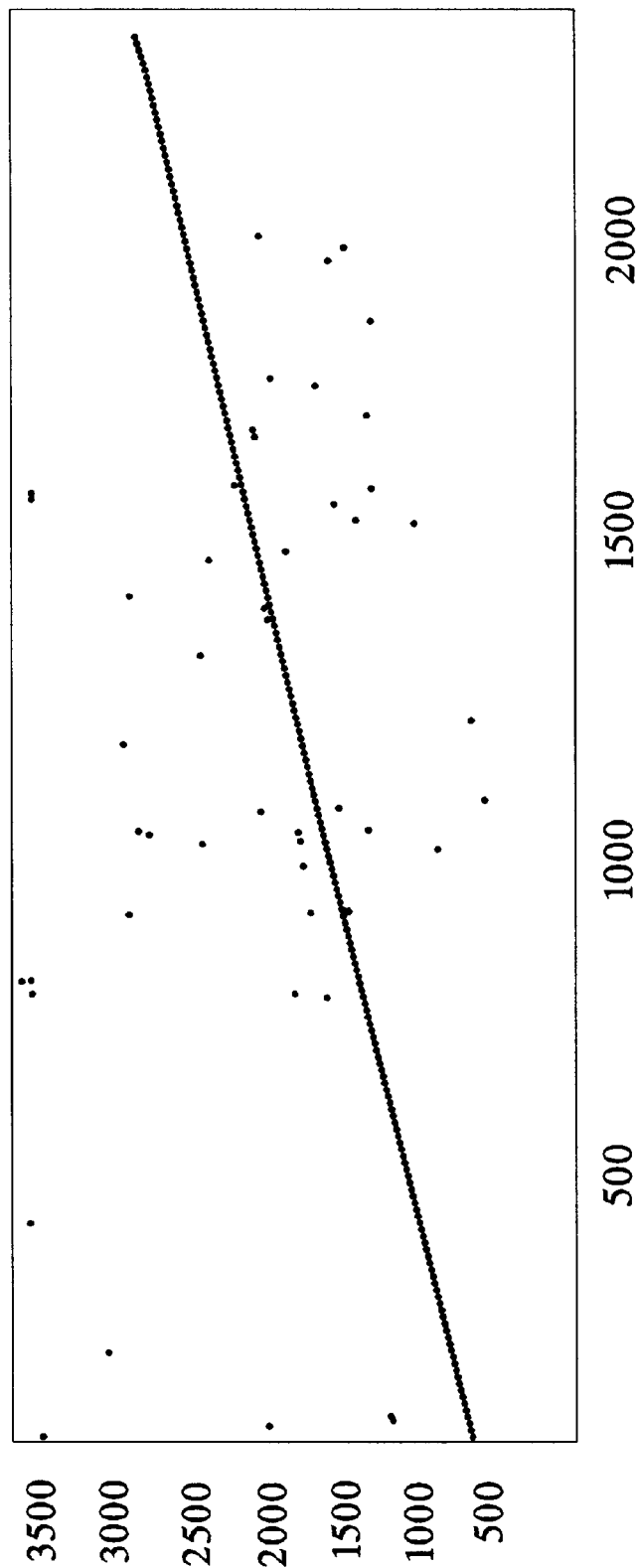
FIGS. 13A through 13D show the dot matrix alignments of khcs protein sequence deduced from the nucleotide sequence in FIG. 12 with kinesin heavy chain sequences from human (FIG. 13A), mouse (FIG. 13B), squid (FIG. 13C) or the portion of mouse khcs encoded by the anti-khcs GSE (FIG. 13D).
Figure 13B:
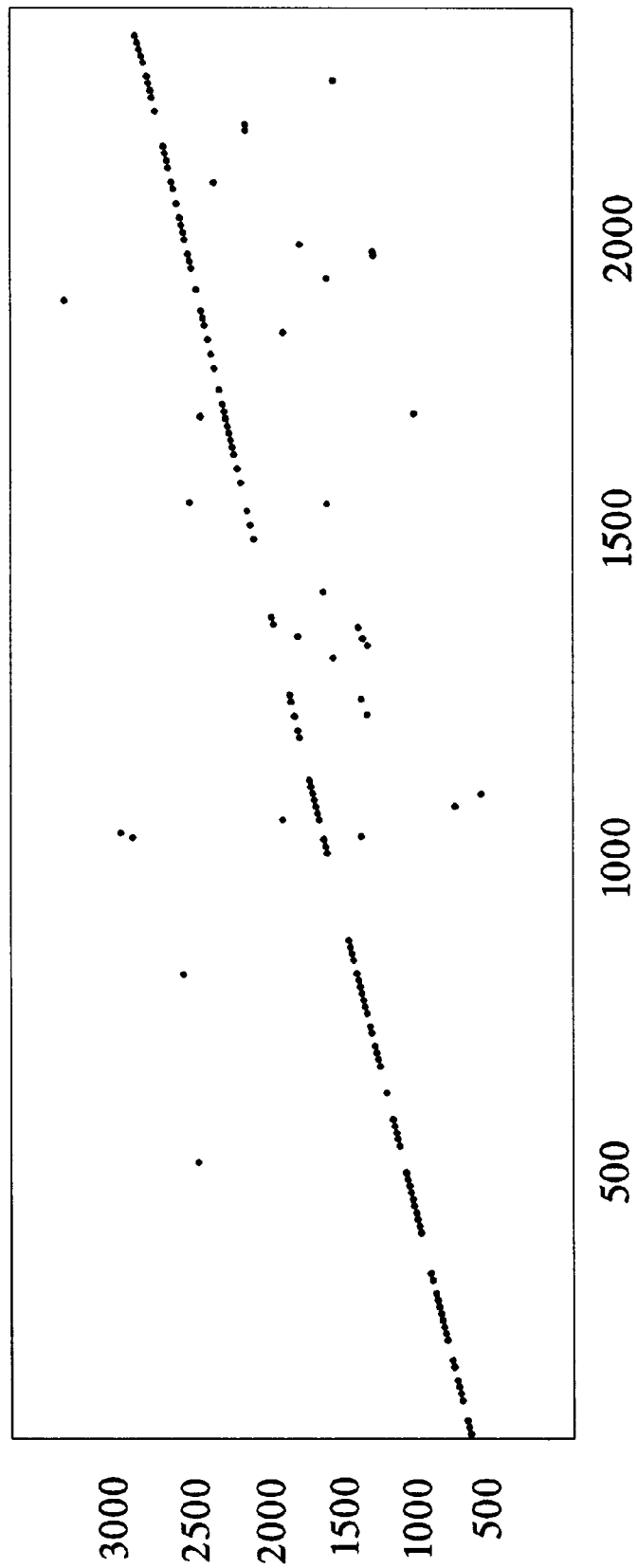
Figure 13C:
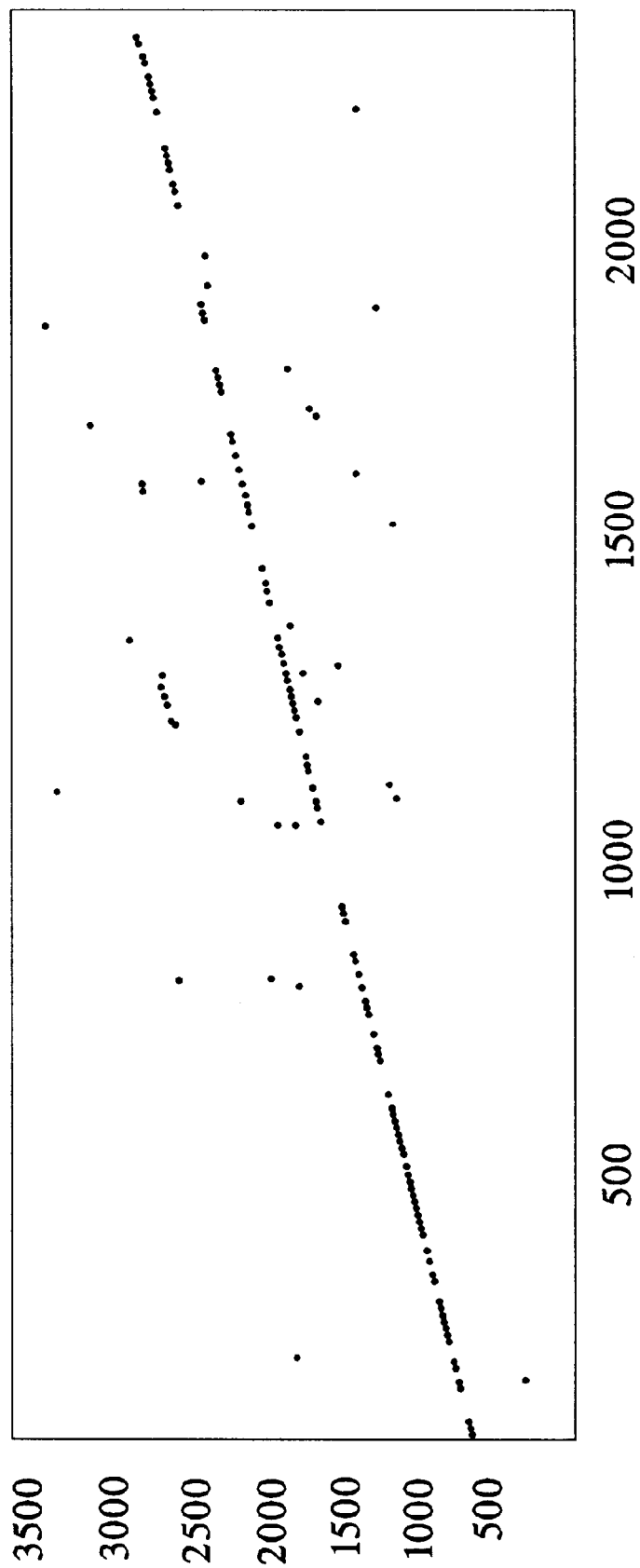
Figure 13D:
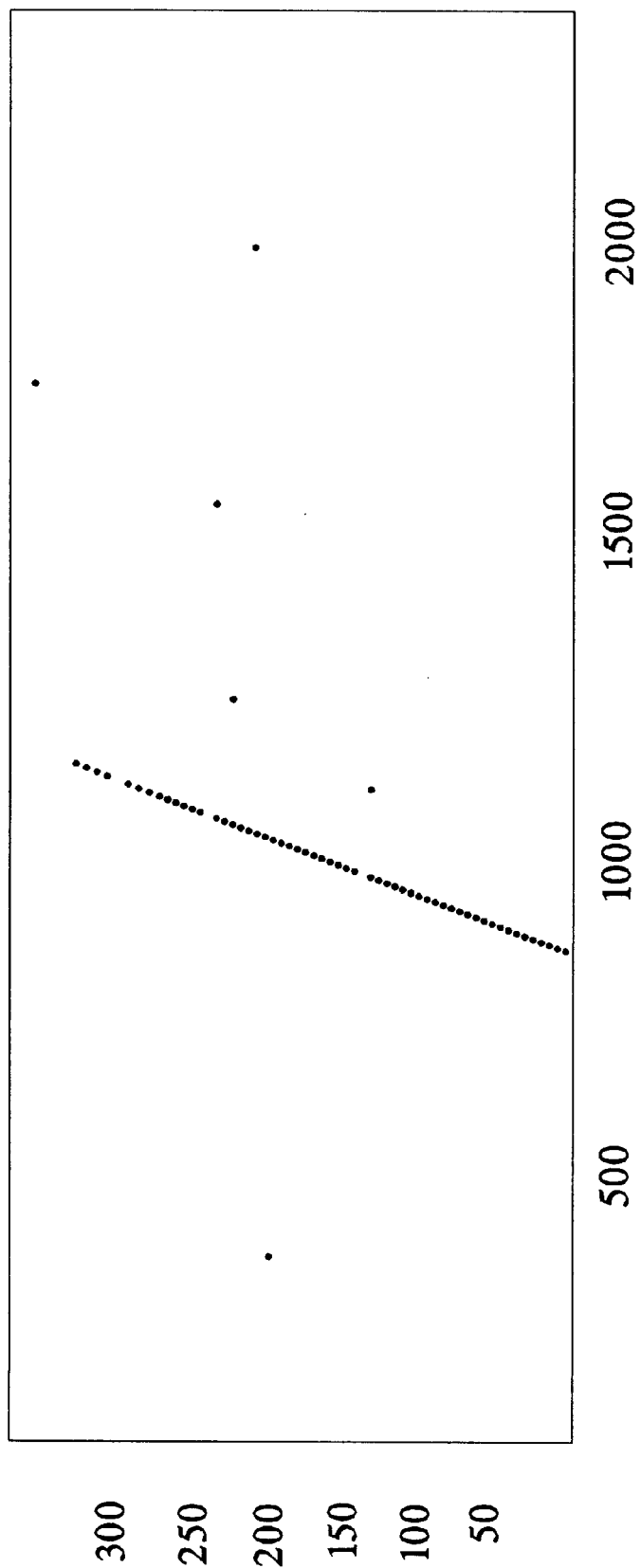
Figure 14A:
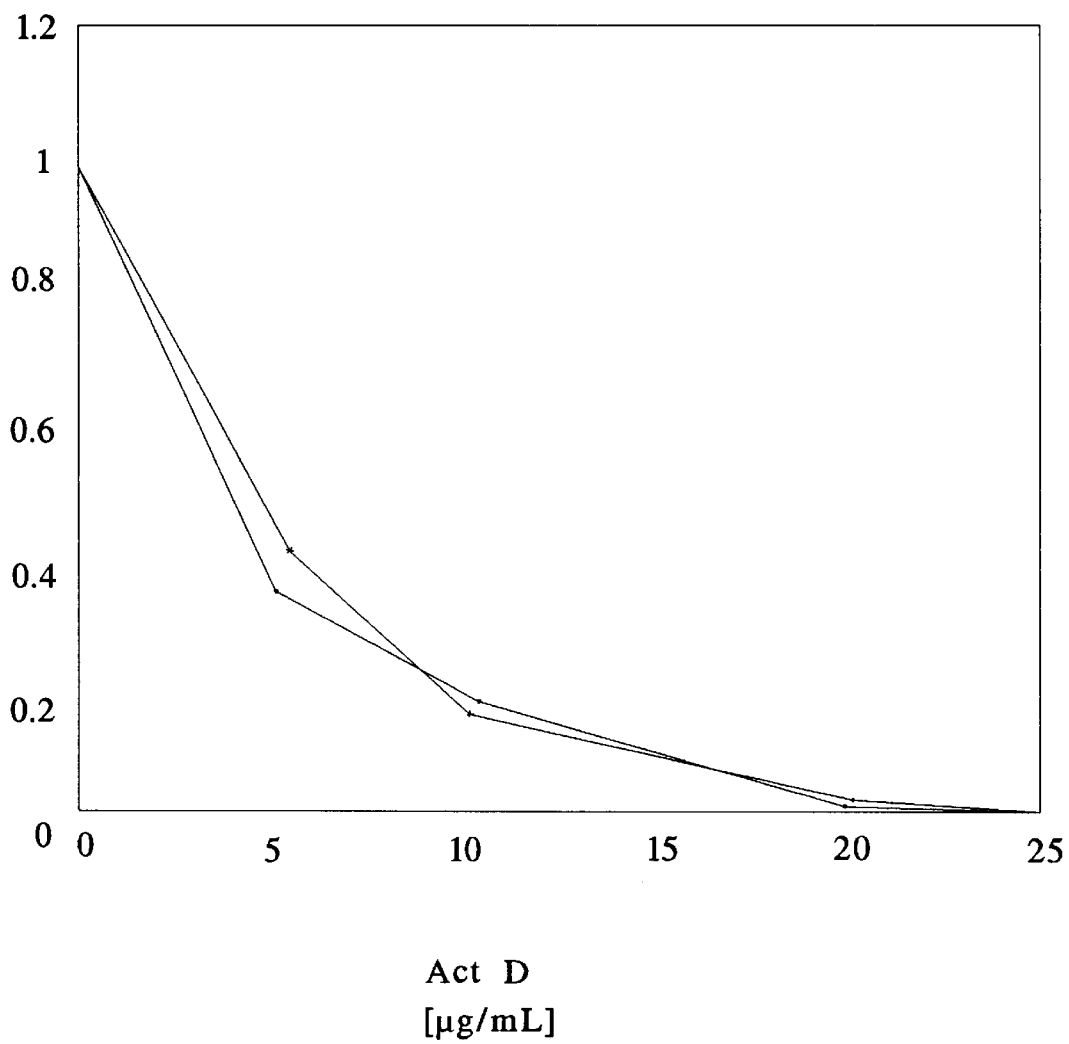
FIGS. 14A through 14F shows the plating efficiency in the presence of various chemotherapeutic drugs of NIH 3T3 cells infected with the LNCX vector (indicated by crosses) or with the LNCX vector containing the anti-khcs GSE (indicated by dots).
Figure 14B:
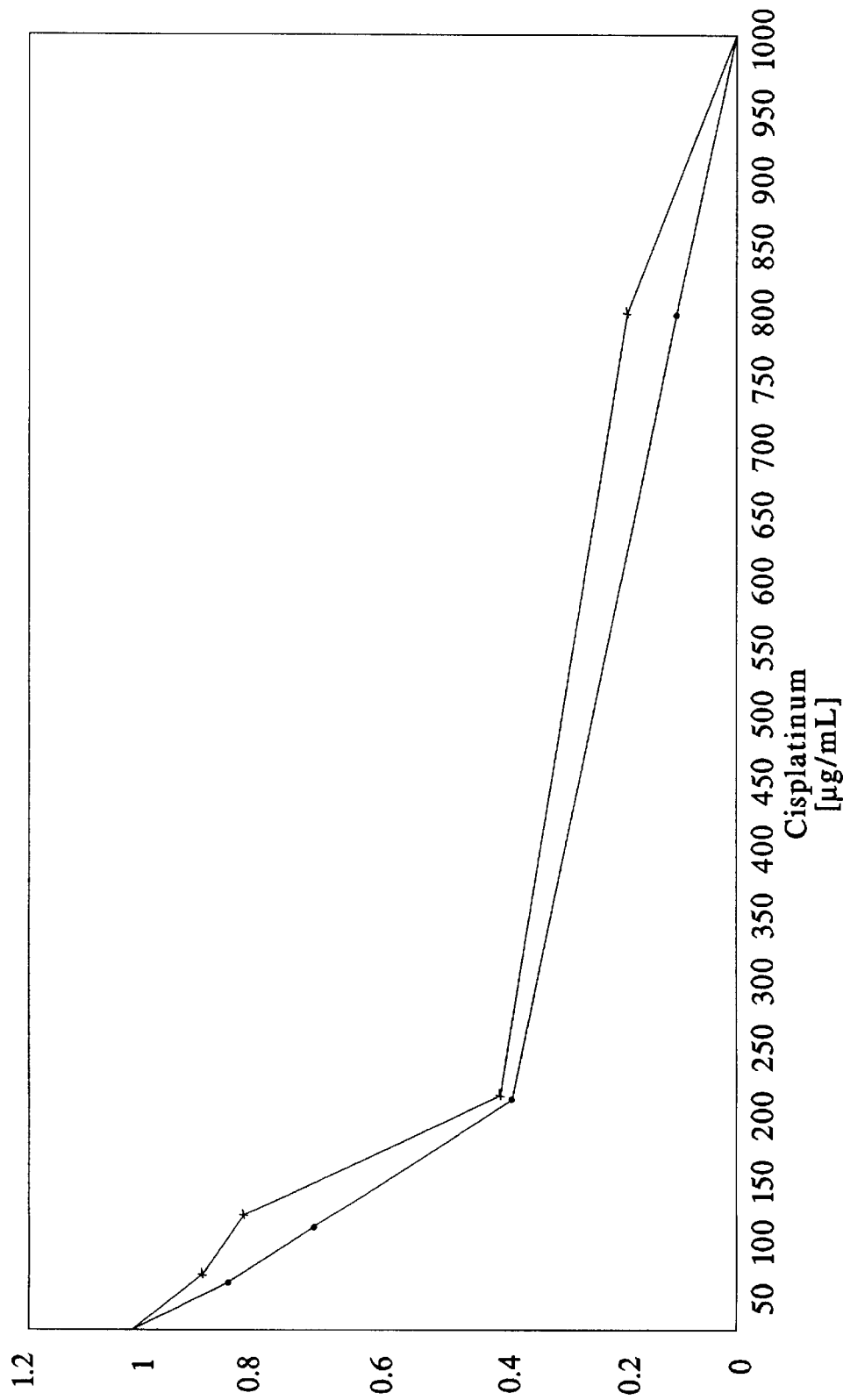
Figure 14C:
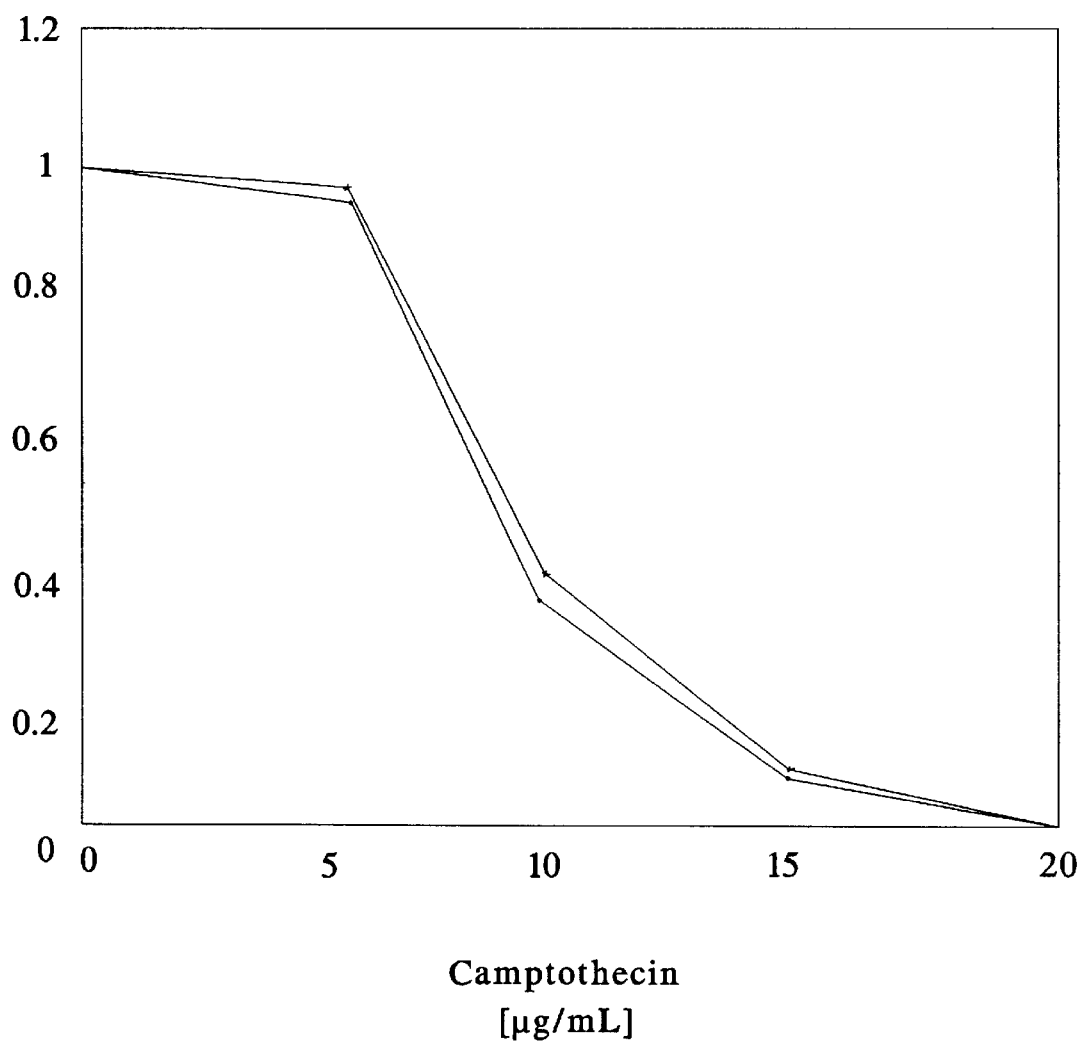
Figure 14D:
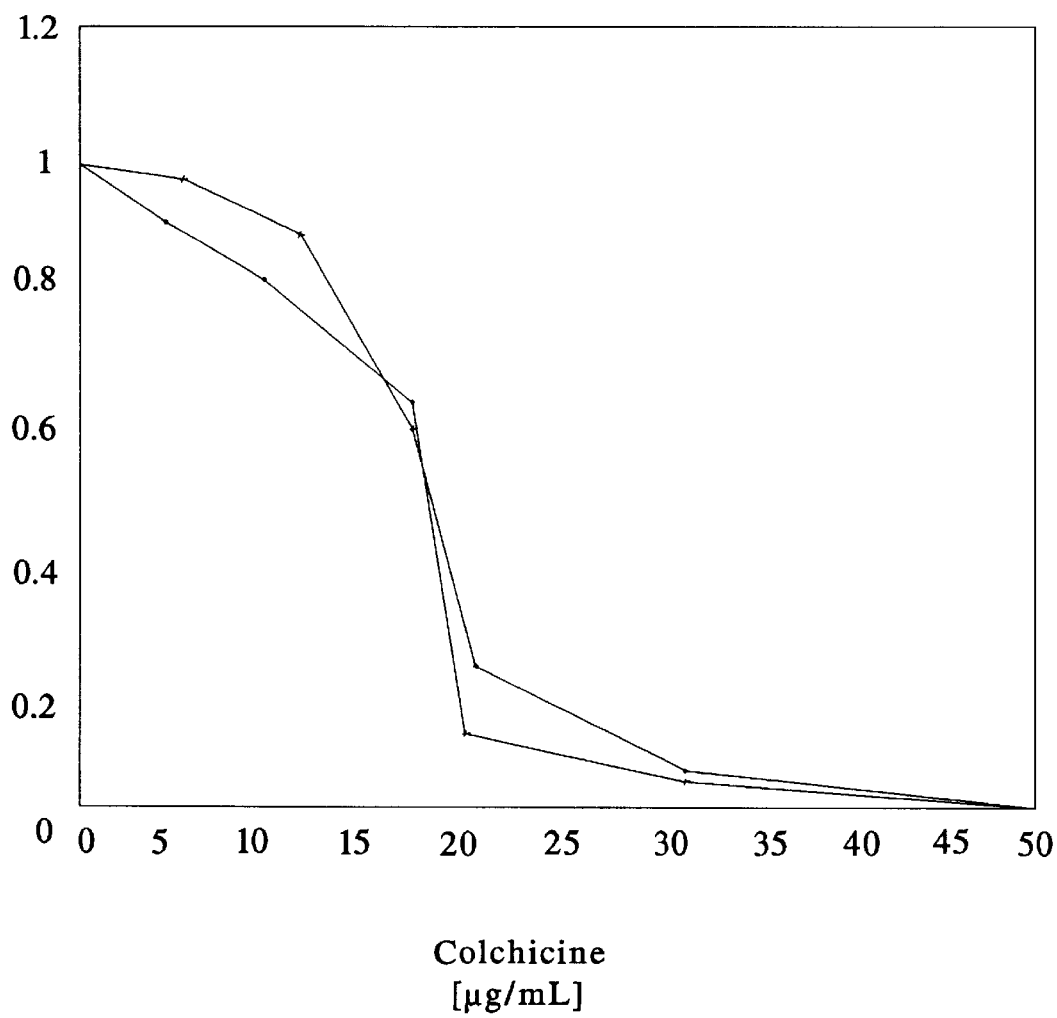
Figure 14E:
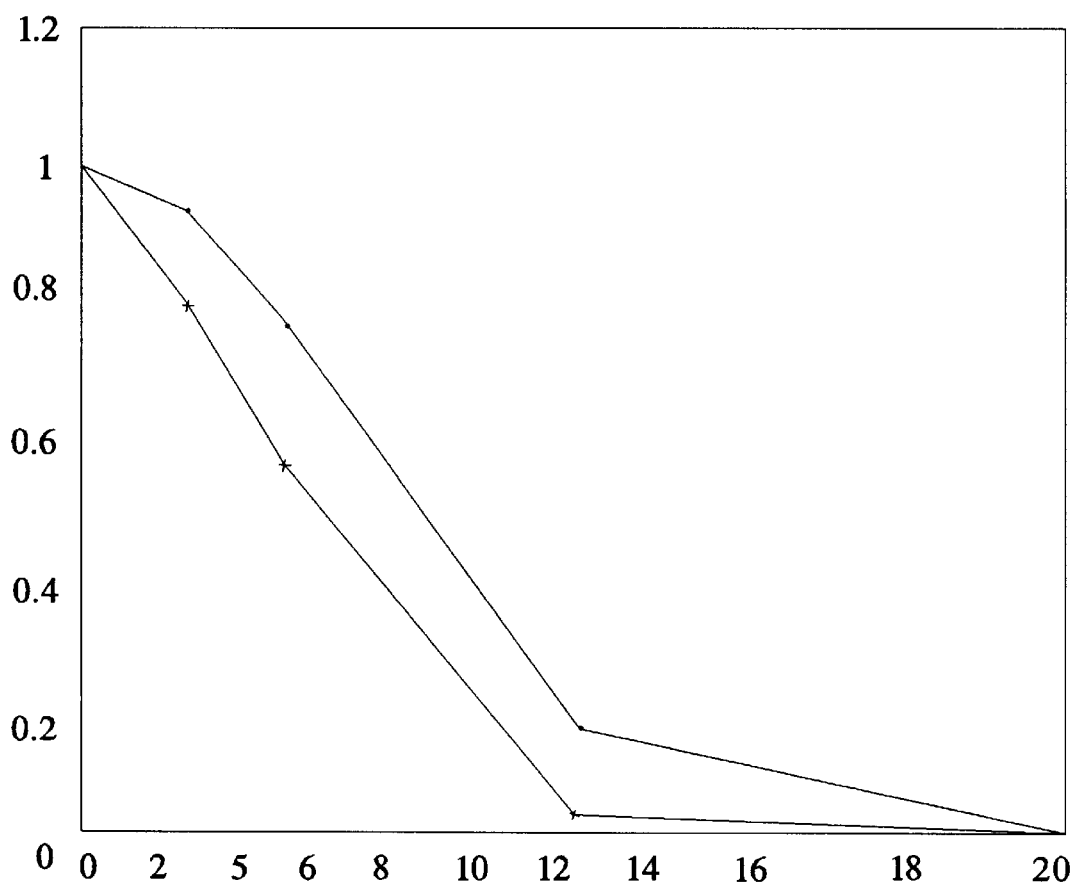
Figure 14F:
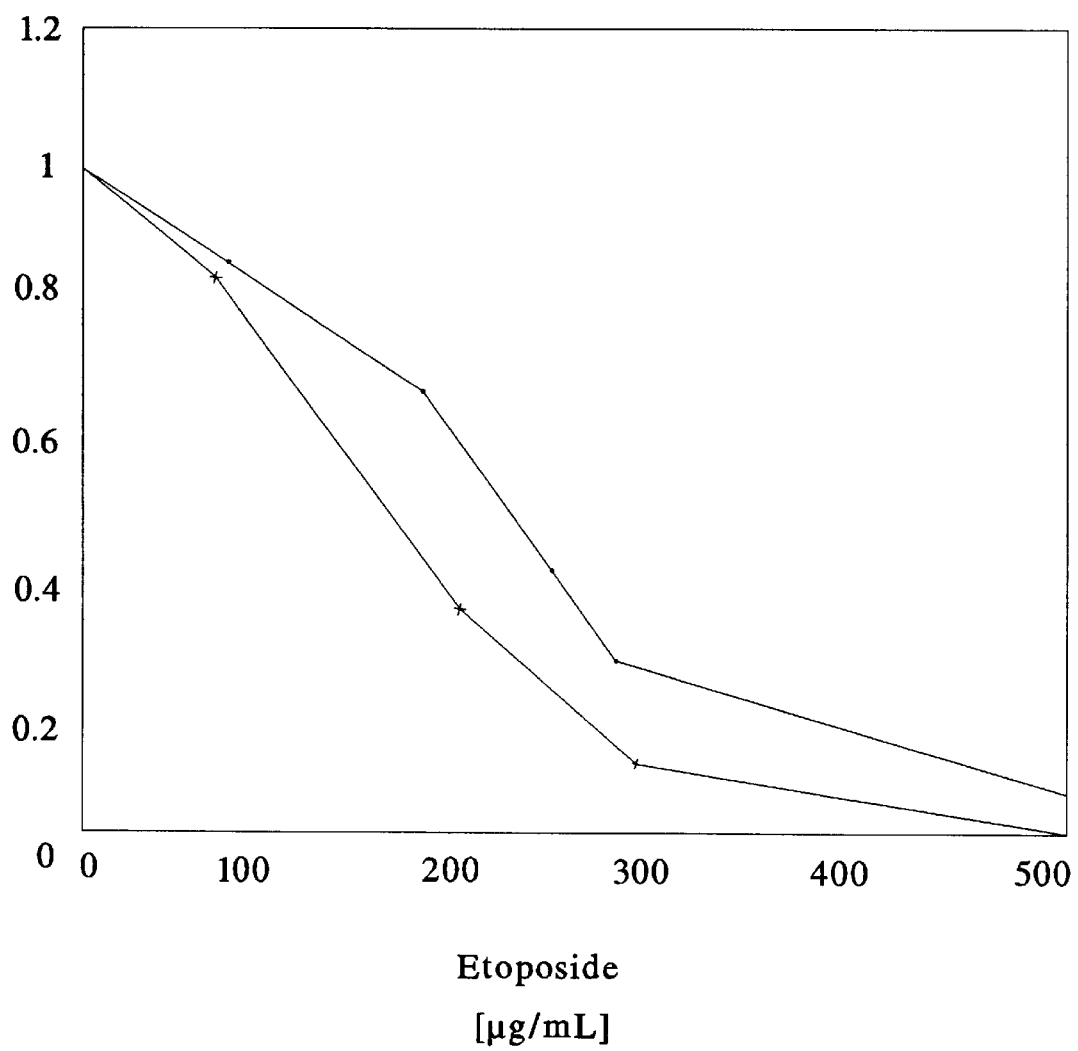

The proviral inserts contained in the etoposide-selected NIH 3T3 cells were analyzed by PCR. This analysis (see FIG. 5B) showed an enrichment for specific fragments, relative to the unselected population of the infected cells. Individual PCR-amplified fragments were recloned into the LNCX vector in the same position and orientation as in the original plasmid, as illustrated in FIG. 6. A total of 42 proviral inserts, enriched after etoposide selection, were thus recloned, and tested either in batches or individually for the ability to confer increased etoposide resistance after retroviral transduction into NIH 3T3 cells. Three non-identical clones were found to induce etoposide resistance, indicating that they contained biologically active GSEs. Etoposide resistance induced by these clones is illustrated in FIGS. 7A and 7B and FIGS. 8A and 8B. These GSEs were named anti-khcs, VPA and VP9-11.

The ability of one of these GSEs (anti-khcs) to induce etoposide resistance was further documented by using the isopropyl β-D-thiogalactopyranoside (IPTG)-inducible promoter/activator system, as described by Baim et al., Proc. Natl. Acad. Sci. USA 88:5072–5076 (1991). The components of this system include an enhancer-dependent promoter, combined in cis with multiple repeats of the bacterial lac operator, and a gene expressing LAP267, an artificial regulatory protein derived from the lac repressor and a mammalian transcriptional activator. The anti-khcs GSE was cloned into the plasmid pX6.CLN, which contains the inducible promotor used by Baim et al., supra. (a gift of Dr. T. Shenk) which expresses the inserts from an enhancer-less SV40 early gene promoter supplemented with 21 repeats of the lac operator sequence. The resulting plasmid, which contains no selectable markers, was co-transfected into NIH 3T3 cells together with the LNCX plasmid carrying the neo gene. The mass population of G418-selected transfectants, along with control cells transfected with the insert-free vector, was exposed to increasing concentrations of etoposide, in the presence or in the absence of 5 mM IPTG. Even though the co-transfection protocol usually leads to the integration of the GSE in only a fraction of the G418-resistant cells, transfection with anti-khcs resulted in a clearly increased etoposide resistance, which was dependent on IPTG (see FIGS. 8A and 8B).

EXAMPLE 5

Sequence Analysis of GSEs Conferring Resistance to the Chemotherapeutic Drug Etoposide The GSEs anti-khcs, VPA, and VP9-11, cloned as described in Example 4, were sequenced by the standard dideoxy sequencing procedure, and the deduced sequences are shown in FIGS. 9–11. The nucleotide sequences of the "sense" and "antisense" strands, as well as amino acid sequences of the peptides encoded by these strands, were analyzed for homology to the nucleic acid and protein sequences present in the National Center for Biotechnology Information data base, using the BLAST network program for homology search. No significant homology with any sequence was detected for the GSEs VPA and VP9-11. IN contrast, the sequence corresponding to the "antisense" strand of the anti-khcs GSE, showed strong homology with several genes encoding the heavy chain of kinesins, a family of microtubule motor proteins involved in intracellular movement of organelles or macromolecules along the microtubules of eukaryotic cells. This protein family has been reviewed by Endow, Trends Biochem. Sci. 16:221–225 (1991). The highest homology was found with the human kinesin heavy chain (KHC) gene, as described by Navone et al., J. Cell Biol. 177:1263–1275 (1992). Anti-khcs therefore encodes antisense RNA for a mouse khc gene, which we term khcs for khc associated with sensitivity (to drugs) or senesence. We refer to the kinesin molecule, formed by the associated of the Khcs protein with kinesin light chains, as kinesin-S, to distinguish it from the other kinesins present in mammalian cells. These results demonstrate that chemotherapeutic drug selection for GSEs can lead to the discovery of novel genetic elements, and can also reveal roles of genes in drug sensitivity that had never before been suspected.

EXAMPLE 6

Cloning and Analysis of the Gene from which Anti-khcs GSE Gene was Derived

The anti-khcs GSE isolated in Example 4 was used as a probe to screen 400,000 clones from each of two cDNA libraries in the lambda gt10 vector. These libraries were prepared by conventional procedures from the RNA of mouse BALB/c 3T3 cells, either unsychronized or at G0→G1 transistion, as described by Lan and Nathans, EMBO J. 4:3145–3531 (1985) and Proc. Natl. Acad. Sci. USA 84:1182–1186 (1987) (a gift of Dr. L. Lau). Screening of the first library yielded no hybridizing clones, but two different clones from the second library were found to contain anti-khcs sequences. These clones were purified and sequenced. Sequence analysis showed that we have isolated the bulk of the mouse khcs cDNA, corresponding to 796 codons (the full-length human KHC cDNA encodes 963 amino acids). This sequence is shown in FIGS. 12A through 12C. The missing 5' and 3' terminal sequences are currently being isolated using the "anchored PCR" technique, as described by Ohara et al., Proc. Natl. Acad. Sci. USA 86:5673–5677 (1989).

The dot-matrix alignment of the sequenced portion of the khcs protein with previously cloned KHC proteins from the human (see Navone et al., J. Cell. Biol. 117:1263–1275 (1992)), mouse (see Kato, J. Neurosci. 2:704–711 (1991)) and squid (see Kosik et al., J. Biol. Chem. 265:3278–3283 (1990)) is shown in FIGS. 13A through 13D. The portion corresponding to the anti-khcs GSE, is shown in FIG. 9. The khcs gene is most highly homologous to the human gene (97% amino acid identity), suggesting that the human KHC (KHCS) gene is functionally equivalent to the mouse khcs. The alignment also shows that the anti-khcs GSE corresponds to the region which is the most highly diverged between different kinesins. This result suggests that the anti-khcs GSE is an antisense-oriented GSE fragment with an inhibitory effect specific to kinesin-S and not to the other mouse kinesins. This suggests the possibility that suppression of the other members of the kinesin family would have a detrimental effect on cell growth, thus resulting in selective isolation of the most specific sequence within the khcs gene.

EXAMPLE 7

Assessment of Drug Cross-Resistance Conferred by Resistance to Etoposide

To determine the spectrum of drugs to which the anti-khcs GSE would confer resistance, we have developed a stable population of ecotropic packaging cells producing the LNCX virus with the anti-khcs insert. This virus was used to infect NIH 3T3 cells. Two days after infection, the cells were analyzed for resistance to several different drugs, relative to control cells infected with the LNCX vector virus, using the standard plating efficiency assay. FIGS. 14A through 14F shows one out of three sets of experiments carried out with different drugs by this assay. Cells infected with the anti-khcs virus showed a clear increase in their resistance to etoposide and Adriamycin relative to control NIH 3T3 cells infected with the control LNCX virus. No changes in resistance were observed with colchicine, cisplatin, camptothecin, or actinomycin D. These latter results remain preliminary, however, because this assay, analyzing total unselected virus-infected populations in relatively insensitive, compared with analysis of highly expressing individually-selected clones. Overall, these results demonstrate that selection of GSEs that confer resistance to one chemotherapeutic drug can result in obtaining GSEs that confer resistance to additional chemotherapeutic drugs.

EXAMPLE 8

Assessment of Cellular Effects of GSEs that Confer Resistance to Etoposide

The virus carrying the anti-khcs GSE was tested for the ability to increase the life span of primary mouse embryo fibroblasts (MEF). MEF were prepared from 10 day old mouse embryos by a standard trypsinization procedure and senescent cells were frozen at different passages prior to crisis. Senescent MEF, two weeks before crisis, were infected with recombinant retroviruses carrying LNCX vector either without an insert or with anti-khcs. FIG. 15 shows MEF cell colonies two weeks after crisis. Relative to uninfected MEF cells, or cells infected with a control LNCX virus, cells infected with anti-khcs showed a great increase in the proportion of cells surviving the crisis. Post-crisis cells infected with the anti-khcs virus showed no microscopically visible features of neoplastic transformation. These results indicate that anti-khcs promotes the immortalization of normal senescent fibroblasts. These results suggest that the normal function of kinesin-S may be associated with the induction of programmed cell death occurring after exposure to certain cytotoxic drugs or in the course of cellular senescence. These results also indicate that isolation of GSEs that confer resistance to chemotherapeutic drugs can provide insight into the cellular genes and processes involved in cell growth regulation.

EXAMPLE 9

Assessment of the Role of Decreased khcs Gene Expression in Naturally Occurring Mechanisms of Drug Resistance To test whether decreased khcs gene expression is associated with any naturally occurring mechanisms of drug resistance, an assay was developed for measuring khcs mRNA levels by cDNA-PCR. This assay is a modification of the quantitative assay described by Noonan et al., Proc. Natl. Acad. Sci. USA 87:7160–7164 (1990) for determining mdr-1 gene expression. The oligonucleotide primers had the sequences AGTGGCTGGAAAACGAGCTA [SEQ. ID. No. 19] and CTTGATCCCTTCTGGTTGAT [SEQ. ID. No. 20]. These primers were used to amplify a 327 bp segment of mouse khcs cDNA, corresponding to the anti-khcs GSE. These primers efficiently amplified the mouse cDNA template but not the genomic DNA, indicating that they spanned at least one intron in the genomic DNA. Using these primers, we determined that khcs mRNA is expressed at a higher level in the mouse muscle tissue than in the kidney, liver or spleen.

In another experiment a pair of primers amplifying a homologous segment of the human KHCS cDNA was selected, based on the reported human KHC sequence published by Navone et al., J. Cell. Biol. 117:1263–1275 (1992). The sequences of these primers are AGTGGCTTGAAAAT-GAGCTC [SEQ. ID. No. 21] and CTTGATCCCTTCTGG-TAGATC [SEQ. ID. No. 22], and they amplify a 327 bp cDNA fragment. These primers were used to test for changes in the KHCS gene expression in several independently isolated populations of human HeLa cells, each selected for spontaneously acquired etoposide resistance. $\beta_2$-microglobulin cDNA sequences were amplified as an internal control. FIG. 16 shows the results of the cDNA-PCR assay on the following population: CX(0), HeLa population infected with the LNCX vector virus and selected with G418; CX (200), the same cells selected for resistance to 200 ng/ml etoposide; $\Sigma 11(0)$, 6(0) and $\Sigma 21(0)$, populations obtained after infection of HeLa cells with recombinant retroviruses carrying different GSEs derived from topoisomerase αcDNA, as described in Example 1, and selected with G418: $\Sigma 11(1000)$, 6(1000) and $\Sigma 21(1000)$, the same populations selected for resistance to 1 μg/ml etoposide. As shown in FIG. 16, the yield of the PCR product specific for the khcs gene was significantly lower in each of the etoposide-selected populations than in the control cells. This result indicates that a decrease in the khcs gene expression is a common natural mechanism for drug resistance.

---

We claim:

1. An antibody raised against a synthetic peptide having an amino acid sequence corresponding to from about 6 amino acids to all of the amino acid sequence encoded by a genetic suppressor element (GSE) produced according to a method for identifying genetic suppressor elements that confer a selectable phenotype upon a eukaryotic cell, wherein the method comprises the steps of:

(a) synthesizing randomly fragmented cDNA prepared from the total mRNA of a cell to yield DNA fragments;

(b) transferring the DNA fragments to an expression vector to yield a genetic suppressor element library, wherein each of the DNA fragments is operatively linked to a protein translation initiation codon, and wherein the expression vector expresses the DNA fragments in a living eukaryotic cell that is capable of exhibiting the selectable phenotype;

(c) genetically modifying living cells by introducing the genetic suppressor element library into the living eukaryotic cells;

(d) isolating or enriching for genetically modified living eukaryotic cells containing genetic suppressor elements that confer the selectable phenotype by selecting cells that express the selectable phenotype;

(e) obtaining the genetic suppressor element from the genetically modified cells, wherein said antibody is specific for an epitope comprising a genetic suppressor element that is not antigenic in the wildtype cellular protein from which the GSE is derived.

2. An antibody according to claim 1 wherein the GSE corresponding to the synthetic peptide is a sense-oriented GSE encoding a peptide.

3. An antibody raised against a synthetic peptide having an amino acid sequence corresponding to from about 6 amino acids to all of the amino acid sequence encoded by a genetic suppressor element (GSE) produced according to a method for identifying genetic suppressor elements corresponding to genes that when suppressed by GSEs, confer a selectable phenotype upon a eukaryotic cell, wherein the method comprises the steps of:

(a) obtaining genomic DNA or a total mRNA population from the cells;

(b) randomly fragmenting the genomic DNA or synthesizing randomly fragmented cDNA from the total mRNA to produce a population of randomly fragmented DNA fragments;

(c) ligating the randomly fragmented DNA fragments to synthetic adaptors to produce amplifiable random DNA fragments;

(d) amplifying the amplifiable random DNA fragments to provide a mixture of amplified DNA fragments;

(e) cloning the mixture of amplified DNA fragments into a suitable expression vector to produce a random fragment expression library;

(f) transferring the random fragment expression library into appropriate target cells;

(g) isolating or enriching for genetically modified living cells containing a selectable phenotype-conferring genetic suppressor element by selecting or enriching for cells that express the selectable phenotype; and (h) recovering the GSE from the target cell having the selectable phenotype, wherein said antibody is specific for an epitope comprising a genetic suppressor element that is not antigenic in the wildtype cellular protein from which the GSE is derived.

4. An antibody according to claim 3 wherein the GSE corresponding to the synthetic peptide is a sense-oriented GSE encoding a peptide.

5. An antibody according to claim 1 wherein the GSE confers the selectable phenotype of resistance in a eukaryotic cell to one or more chemotherapeutic drugs.

6. An antibody according to claim 1 wherein the synthetic peptide having an amino acid sequence comprising from about 6 to all of the amino acids encoded by a GSE identified by Seq. ID Nos. 2, 3, 4, 5, 9, 10, 12, 13, 16 or 17.

7. A synthetic peptide having an amino acid sequence comprising from about 6 to all of the amino acids encoded by a GSE identified by Seq. ID Nos. 2, 3, 4, 5, 9, 10, 12, 13, 16 or 17.

* * * * *

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 164 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:1:

```
GTGTCTGGGC GGAGCAAAAT ATGTTCCAAT TGTGTTTTCT TTTGATAGAT TCTTTCAACA        60

GACAGTCTTT TCTTAGCATC TTCATTTTTC TTTATTTTGT TGACTTGCAT ATTTTCATTT       120

ACAGGCTGCA ATGGTGACAC TTCCATGGTG ACGGTCGTGA AGGG                        164
```

(2) INFORMATION FOR SEQ ID NO:2:

(i) SEQUENCE CHARACTERISTICS:
      (A) LENGTH: 213 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:2:

```
TGAAAAGATG TATGTCCCAG CTCTCATATT TGGACAGCTC CTAACTTCTA GTAACTATGA        60

TGATGATGAA AAGAAAGTGA CAGGTGGTCG AAATGGCTAT GGAGCCAAAT TGTGTAACAT       120

ATTCAGTACC AAATTTACTG TGGAAACAGC CAGTAGAGAA TACAAGAAAA TGTTCAAACA       180

GACATGGATG GATAATATGG GAAGAGCTGG TGA                                   213
```

(2) INFORMATION FOR SEQ ID NO:3:

(i) SEQUENCE CHARACTERISTICS:
      (A) LENGTH: 181 base pairs
      (B) TYPE: nucleic acid
      (C) STRANDEDNESS: single (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

GCCCATTGGT CAGTTTGGTA CCAGGCTACA TGGTGGCAAG GATTCTGCTA GTCCACGATA      60

CATCTTTACA ATGCTCAGCT CTTTGGCTCG ATTGTTATTT CCACCAAAAC ATGATCACAC     120

GTTGAAGTTT TTATATGATG ACAACCAGCG TGTTGAGCCT GAATGGTACA TTCCTATTAT     180

T                                                                    181

(2) INFORMATION FOR SEQ ID NO:4:

(i) SEQUENCE CHARACTERISTICS:
        (A) LENGTH: 224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

TGAATGGTAC ATTCCTATTA TTCCCATGGT GCTGATAAAT GGTGCTGAAG GAATCGGTAC      60

TGGGTGGTCC TGCAAAATCC CCAACTTTGA TGTGCGTGAA ATTGTAAATA ACATCAGGCG     120

TTTGATGGAT GGAGAAGAAC CTTTGCCAAT GCTTCCAAGT TACAAGAACT TCAAGGGTAC     180

TATTGAAGAA CTGGCTCCAA ATCAATATGT GATTAGTGGT GAAG                     224

(2) INFORMATION FOR SEQ ID NO:5:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

TGCGTGAAAT TGTAAATAAC ATCAGGCGTT TGATGGATGG AGAAGAACCT TGCCAATGC       60

TTCCAAGTTA CAAGAACTTC AAGGGTACTA TTGAAGAACT GGCTCCAAAT CAATATGTGA     120

TTAGTGGTGA AGTAGCTATT CTTAATTCTA CAACCATTGA AATCTCAGAG CTTCCCGTCA     180

GAACATGGAC CCAGACATAC AAAGAACAAG TTCTAGAACC CATGTTGAAT GGCACCGAGA     240

AGACACCTCC TCTCATAACA GACTATAGGG AATACCATAC AGATACCACT GTGAAATTTG     300

TTGTGAAGAT GACTGAAGAA AAACTGGCA                                      329

(2) INFORMATION FOR SEQ ID NO:6:

(i) SEQUENCE CHARACTERISTICS:
        (A) LENGTH: 194 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

| | |
|---|---:|
| CACTCTTTTC AGTTTCCTTT TCGTTGTCAC TCTCTTCATT TTCTTCTTCA TCTGGAACCT | 60 |
| TTTGCTGGGC TTCTTTCCAG GCCTTCACAG GATCCGAATC ATATCCCCTC TGAATCAGAA | 120 |
| CTTTAATTAA TTCTTTCTTA GGCTTATTTT CAATGATTAT TTTGCCATCT ATTTTCTCAT | 180 |
| AGATAAAGCG AGCC | 194 |

(2) INFORMATION FOR SEQ ID NO:7:

(i) SEQUENCE CHARACTERISTICS:
(A) LENGTH: 206 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:7:

| | |
|---|---:|
| TCTGCCTCTG CTTTCATTTC TATGGTTATT CGTGGAATGA CTCTTTGACC ACGCGGAGAA | 60 |
| GGCAAAACTT CAGCCATTTG TGTTTTTTTC CCCTTGGCCT TCCCCCCTTT CCCAGGAAGT | 120 |
| CCGACTTGTT CATCTTGTTT TTCCTTGGCT TCAACAGCCT CCAATTCTTC AATAAATGTA | 180 |
| GCCAAGTCTT CTTTCCACAA ATCTGA | 206 |

(2) INFORMATION FOR SEQ ID NO:8:

(i) SEQUENCE CHARACTERISTICS:
(A) LENGTH: 194 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:8:

| | |
|---|---:|
| GACACGACAC TTTTCTGTGG TTTCAGTTCT TTGTTACTAA GTTTTGGGGA AGTTTTGGTC | 60 |
| TTAGGTGGAC TAGCATCTGA TGGGACAAAA TCTTCATCAT CAGTTTTTTC ATCAAAATCT | 120 |
| GAGAAATCTT CATCTGAATC CAAATCCATT GTGAATTTTG TTTTTGTTGC TGCTCTCCGT | 180 |
| GGCTCTGTTT CTCG | 194 |

(2) INFORMATION FOR SEQ ID NO:9:

(i) SEQUENCE CHARACTERISTICS:
(A) LENGTH: 242 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

| | | |
|---|---|---|
| CTGAAACCAC AGAAAAGTGT CGTGTCAGAC CTTGAAGCTG ATGATGTTAA GGGCAGTGTA | 60 |
| CCACTGTCTT CAAGCCCTCC TGCTACACAT TTCCCAGATG AAACTGAAAT TACAAACCCA | 120 |
| GTTCCTAAAA AGAATGTGAC AGTGAAGAAG ACAGCAGCAA AAAGTCAGTC TTCCACCTCC | 180 |
| ACTACCGGTG CCAAAAAAAG GGCTGCCCCA AAAGGAACTA AAAGGGATCC AGCTTTGAAT | 240 |
| TC | 242 |

(2) INFORMATION FOR SEQ ID NO:10:

(i) SEQUENCE CHARACTERISTICS:
      (A) LENGTH: 341 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:10:

| | | |
|---|---|---|
| AACCAGCGTG TTGAGCCTGA ATGGTACATT CCTATTATTC CCATGGTGCT GATAAATGGT | 60 |
| GCTGAAGGAA TCGGTACTGG GTGGTCCTGC AAAATCCCCA ACTTTGATGT GCGTGAAATT | 120 |
| GTAAATAACA TCAGGCGTTT GATGGATGGA GAAGAACCTT TGCCAATGCT TCCAAGTTAC | 180 |
| AAGAACTTCA AGGGTACTAT TGAAGAACTG GCTCCAAATC AATATGTGAT TAGTGGTGAA | 240 |
| GTAGCTATTC TTAATTCTAC AACCATTGAA ATCTCAGAGC TTCCCGTCAG AACATGGACC | 300 |
| CAGACATACA AAGAACAAGT TCTAGAACCC ATGTTGAATG G | 341 |

(2) INFORMATION FOR SEQ ID NO:11:

(i) SEQUENCE CHARACTERISTICS:
      (A) LENGTH: 220 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:11:

| | | |
|---|---|---|
| AATTCAAAGC TGGATCCCTT TTAGTTCCTT TTGGGGCAGC CCTTTTTTTG GCACCGGTAG | 60 |
| TGGAGGTGGA AGACTGACTT TTTGCTGCTG TCTTCTTCAC TGTCACATTC TTTTTAGGAA | 120 |
| CTGGGTTTGT AATTTCAGTT TCATCTGGGA AATGTGTAGC AGGAGGGCTT GAAGACAGTG | 180 |
| GTACACTGCC CTTAACATCA TCAGCTTCAA GGTCTGACAC | 220 |

(2) INFORMATION FOR SEQ ID NO:12:

(i) SEQUENCE CHARACTERISTICS:
      (A) LENGTH: 170 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:12:

GTGTTGAGCC TGAATGGTAC ATTCCTATTA TTCCCATGGT GCTGATAAAT GGTGCTGAAG    60

GAATCGGTAC TGGGTGGTCC TGCAAAATCC CCAACTTTGA TGTGCGTGAA ATTGTAAATA   120

ACATCAGGCG TTTGATGGAT GGAGAAGAAC CTTTGCCAAT GCTTCCAAGT              170

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

AATCATCGAT GGATGGATGG                                                20

(2) INFORMATION FOR SEQ ID NO:14:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:14:

CCATCCATCCATCGATGATTAAA                                              23

(2) INFORMATION FOR SEQ ID NO:15:

(i) SEQUENCE CHARACTERISTICS:
            (A) LENGTH: 327 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:15:

CTTGATCCCT TCTGGTTGAT GCCAGAAGCT CTTCCTGATC CAGCATTTGT ATCTTCAATT    60

TCTCTACCAA TTGGCTTTGT TGGTTAATCT CTTCATCCTT GTCATCAAGT TGTTTATACA   120

ATTTAGCAAG TTCTTCTTCA CACTTTCTTC TTTCAGCATC GGTAAAACTA CCAGCCATTC   180

CGACTGCAGC AGCTGGTTTA TCACTGGTAA TAGCAATATC TTTATCCGCT GTGAAGGCTT   240

CCAAATTAGC TTTCTCTTTG TCAAACTGCT CATCAATAGG CACTGTCTCC CCGTTACGCC   300

```
AACGGTTTAG CTCGTTTTCC AGCCACT                                           327

(2) INFORMATION FOR SEQ ID NO:16:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:16:

CCGACCGGGA GCGGGAGAAG GAGCGGGAGC GGGAGCAGCG GGAGAAGGAG CGGGAGAAGG     60

AGCTGGAGCG CGACGGGAGA AGGAACGGGA GCGCGAGCTG GAGCGGCAGC GGGAGCAGCG    120

GGCGAGGGAG AAGGAGCTGC TGGCTGCCAA GGCCTTAGAG CCCACCACCT TCCTGCCTGT    180

GGCCGAGCTG CACGGACTCC GAGGTCACAG CACGGAGGAG CGGCCCAAGC CCTCGGAGCA    240

GCTGACCCCA                                                          250

(2) INFORMATION FOR SEQ ID NO:17:

(i) SEQUENCE CHARACTERISTICS:
        (A) LENGTH: 208 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:17:

CTCAGAGGTG ATCCTCTCGG AGTCGAGCTC AGGAGAAGGA GTCCCCTTCT TTGAGACTTG     60

GATGCAGACC TGCATGTCCG AGGAGGGCAA GATTTTGAAC CCTGACCATC CCTGCTTCCG    120

CCCTGACTCC ACCGAAGTCG AGTCCTTGGT GGCCCTGCTC AACAACTCTT CAGAGATGAA    180

GCTAGTACAG ATGAAGTAGC ACGAGGCC                                      208

(2) INFORMATION FOR SEQ ID NO:18:

(i) SEQUENCE CHARACTERISTICS:
        (A) LENGTH: 2389 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:18:

CGACAAACAT CATCTGGGAA GACCCACACG ATGGAGGGTA AACTTCATGA TCCAGAAGGC     60

ATGGGAATTA TTCCAAGAAT AGTGCAAGAT ATTTTTAATT ATATTTACTC CATGGATGAA    120

AATTTGGAAT TCATATTAA GGTTTCATAT TTTGAAATAT ATTTGGATAA GATAAGGGAC     180

TTGTTAGATG TTTCAAAGAC TAACCTTTCA GTCCATGAAG ACAAAAACCG TGTTCCCTAT    240

GTAAAGGGGT GCACAGAACG TTTCGTGTGT AGTCCAGATG AAGTCATGGA TACCATAGAT    300

GAAGGGAAAT CCAACAGAGA TGTCGCAGTT ACAAATATGA ATGAACATAG CTCTAGGAGC    360
```

```
CACAGCATAT TTCTTATTAA TGTAAAACAA GAGAATACAC AAACGGAACA GAAACTCAGT      420

GGAAAGCTTT ATCTGGTTGA TTTAGCTGGC AGTGAGAAGG TTAGTAAGAC TGGGGCTGAA      480

GGTGCTGTGC TGGATGAAGC TAAGAACATC AAGAAGTCAC TTTCTGCACT TGGAAATGTC      540

ATTTCTGCTT TGGCAGAGGG CAGTACCTAT GTTCCTTATC GAGATAGTAA AATGACCAGA      600

ATTCTTCAAG ATTCATTAGG TGGCAACTGT AGGACCACTA TTGTCATATG CTGCTCTCCA      660

TCATCATACA ATGAGTCTGA GACAAAGTCA ACACTCCTCT TTGGTCAAAG GCCAAAACA       720

ATTAAGAACA CAGTCTGTGT CAATGTAGAG TTAACTGCAG AGCAGTGGAA AAAGAAGTAT      780

GAAAAAGAAA AGGAAAAAAA TAAGACTCTA CGGAACACTA TTCAGTGGCT GGAAAACGAG      840

CTAAACCGTT GGCGTAACGG GGAGACAGTG CCTATTGATG AGCAGTTTGA CAAAGAGAAA      900

GCTAATTTGG AAGCCTTCAC AGCGGATAAA GATACTGCTA TTACCAGTGA TAAACCAGCT      960

GCTGCAGTCG GAATGGCTGG TAGTTTTACC GATGCTGAAA GAAGAAAGTG TGAAGAAGAA     1020

CTTGCTAAAT TGTATAAACA GCTTGATGAC AAGGATGAAG AGATTAACCA ACAAAGCCAA     1080

TTGGTAGAGA AATTGAAGAC ACAAATGCTG GATCAGGAAG AGCTTCTGGC ATCAACCAGA     1140

AGGGATCAAG ATAATATGCA AGCTGAACTG AATCGCCTCC AAGCAGAAAA TGATGCTTCT     1200

AAAGAAGAAG TCAAAGAAGT TTTACAGGCC TTAGAGGAAC TGGCTGTTAA TTATGATCAG     1260

AAGTCTCAGG AAGTTGAAGA CAAAACAAAG GAATATGAAT GCTTAGTGA TGAATTGAAT      1320

CAAAAATCTG CAACTTTAGC AAGTATTGAT GCTGAGCTTC AGAAGCTGAA GGAAATGACC     1380

AACCACCAGA AGAAACGAGC AGCTGAAATG ATGGCATCAT TATTAAAAGA CCTTGCAGAA     1440

ATAGGAATTG CTGTGGGGAA TAACGATGTG AAGCAACCAG AAGGAACTGG TATGATAGAT     1500

GAAGAGTTTA CTGTTGCAAG ACTCTACATT AGCAAAATGA AATCAGAAGT AAAGACCATG     1560

GTGAAACGCT GCAAACAGCT AGAAAGCACG CAGACTGAGA GCAACAAAAA AATGGAAGAA     1620

AATGAGAAAG AGTTAGCAGC ATGCCAGCTT CGGATCTCCC AACATGAAGC CAAAATCAAG     1680

TCACTGACTG AGTACCTTCA GAATGTAGAA CAAAAGAAGA GGCAGCTGGA GGAATCTGTT     1740

GATTCCCTTG GTGAGGAGCT AGTCCAACTC CGAGCACAAG AGAAAGTCCA TGAAATGGAA     1800

AAAGAGCACT TGAACAAGGT TCAGACTGCA AATGAAGTCA AGCAAGCTGT TGAGCAGCAG     1860

ATCCAGAGTC ACAGAGAAAC CCACCAAAAA CAAATCAGTA GCTTGCGAGA TGAAGTTGAG     1920

GCAAAGGAAA AGCTAATCAC TGACCTCCAA GACCAAAACC AGAAGATGGT GTTGGAGCAG     1980

GAACGGCTAA GGGTGGAGCA TGAGAGGCTG AAGGCTACAG ACCAAGAGAA GAGCAGGAAG     2040

CTGCATGAGC TCACGGTTAT GCAAGACAGA CGAGAACAAG CAAGACAAGA CTTGAAGGGT     2100

TTGGAGGAGA CCGTGGCAAA AGAACTTCAG ACTTTACACA ACCTGCGTAA GCTCTTTGTT     2160

CAGGACTTGG CTACCAGGGT GAAAAGAGG CCGAGGTCGA CTCTGACGAC ACTGGCGGCA      2220

GTGCTGCACA GAAGCAGAAA ATCTCCTTCC TTGAAAACAA CCTTGAACAG CTCACCAAAG     2280

TGCACAAGCA GTTGGTACGT GATAATGCAG ATCTTCGCTG TGAGCTTCCT AAGTTAGAGA     2340

AACGGCTTAG AGCTACTGCA GAAAGAGTGA AAGCTTTGGA GTCAGCCCG               2389
```

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA -continued (iii) HYPOTHETICAL: NO (iv) ANTI-SENSE: YES (xi) SEQUENCE DESCRIPTION: SEQ ID NO:19:

AGTGGCTGGA AAACGAGCTA                                           20

(2) INFORMATION FOR SEQ ID NO:20:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:20:

CTTGATCCCT TCTGGTTGAT                                           20

(2) INFORMATION FOR SEQ ID NO:21:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:21:

AGTGGCTTGA AAATGAGCTC                                           20

(2) INFORMATION FOR SEQ ID NO:22:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:22:

CTTGATCCCT TCTGGTAGAT G                                         21